United States Patent
Nabeshima et al.

(10) Patent No.: US 9,364,332 B2
(45) Date of Patent: Jun. 14, 2016

(54) ARTIFICIAL KNEE JOINT IMPLANT

(71) Applicant: KYOCERA MEDICAL CORPORATION, Osaka (JP)

(72) Inventors: Reiko Nabeshima, Osaka (JP); Masahiko Hashida, Osaka (JP)

(73) Assignee: KYOCERA Medical Corporation, Osaka (JP)

( * ) Notice: Subject to any disclaimer, the term of this patent is extended or adjusted under 35 U.S.C. 154(b) by 0 days.

(21) Appl. No.: 14/347,617

(22) PCT Filed: Sep. 20, 2012

(86) PCT No.: PCT/JP2012/074012
§ 371 (c)(1),
(2) Date: Mar. 26, 2014

(87) PCT Pub. No.: WO2013/047310
PCT Pub. Date: Apr. 4, 2013

(65) Prior Publication Data
US 2014/0243989 A1 Aug. 28, 2014

(30) Foreign Application Priority Data
Sep. 27, 2011 (JP) .................................. 2011-210410

(51) Int. Cl.
*A61F 2/38* (2006.01)
*A61F 2/30* (2006.01)

(52) U.S. Cl.
CPC .............. *A61F 2/3836* (2013.01); *A61F 2/3886* (2013.01); *A61F 2002/30604* (2013.01)

(58) Field of Classification Search
CPC ....... A61F 2/3886; A61F 2/3836; A61F 2/38; A61F 2/3868; A61F 2002/38; A61F 2002/30604

USPC ............................................ 623/20.14–20.35
See application file for complete search history.

(56) References Cited

U.S. PATENT DOCUMENTS 5,226,915 A * 7/1993 Bertin ................. A61F 2/30734
623/20.15
6,558,426 B1 * 5/2003 Masini ....................... 623/20.27
(Continued)

FOREIGN PATENT DOCUMENTS

CA 2090191 A1 10/1993
EP 0577529 A1 1/1994
(Continued)

OTHER PUBLICATIONS

International Search Report; PCT/JP2012/074012; Dec. 25, 2012.
(Continued)

*Primary Examiner* — Alvin Stewart
(74) *Attorney, Agent, or Firm* — Studebaker & Backett PC

(57) ABSTRACT

The present invention provides a PS-type artificial knee joint implant, with which the gap balance can be adjusted in order to realize a stable deep flexion movement, the burden on a surgeon and a patient can be reduced, and the patient can perform a natural flexion movement. An artificial knee joint implant 1 includes femoral components, one of which is selected and attached to a distal portion of a femur of the patient, and tibial inserts, one of which is selected and attached to a proximal portion of a tibia of the patient. The femoral components have a cam portion that is disposed between posterior portions of two femoral joint faces, respectively. The tibial inserts have posts that can be brought into contact with the cam portion. The posts have different anteroposterior positions.

5 Claims, 14 Drawing Sheets

(56) References Cited

U.S. PATENT DOCUMENTS

| | | | |
|---|---|---|---|
| 6,589,283 B1* | 7/2003 | Metzger et al. | 623/20.35 |
| 7,678,152 B2 | 3/2010 | Suguro et al. | |
| 8,784,490 B2* | 7/2014 | Wasielewski | A61B 19/46 |
| | | | 623/16.11 |
| 8,790,411 B2* | 7/2014 | Mandell | A61B 17/155 |
| | | | 623/20.15 |
| 9,056,013 B2* | 6/2015 | Faure | A61F 2/3859 |
| 2003/0009230 A1 | 1/2003 | Gundlapalli et al. | |
| 2004/0002767 A1 | 1/2004 | Wyss | 623/20.27 |
| 2004/0162620 A1* | 8/2004 | Wyss | A61F 2/3886 |
| | | | 623/20.27 |
| 2004/0243244 A1 | 12/2004 | Otto et al. | |
| 2005/0209701 A1 | 9/2005 | Suguro et al. | |
| 2008/0027555 A1 | 1/2008 | Hawkins | |
| 2008/0119940 A1 | 5/2008 | Otto et al. | |
| 2010/0042224 A1 | 2/2010 | Otto et al. | |
| 2010/0234961 A1 | 9/2010 | Otto et al. | |
| 2011/0029093 A1* | 2/2011 | Bojarski et al. | 623/20.35 |
| 2011/0125280 A1 | 5/2011 | Otto et al. | |
| 2011/0125281 A1 | 5/2011 | Otto et al. | |
| 2011/0125282 A1 | 5/2011 | Otto et al. | |
| 2011/0125283 A1 | 5/2011 | Otto et al. | |
| 2011/0130841 A1 | 6/2011 | Otto et al. | |
| 2011/0130842 A1 | 6/2011 | Otto et al. | |
| 2011/0130843 A1 | 6/2011 | Otto et al. | |
| 2011/0137426 A1 | 6/2011 | Otto et al. | |
| 2011/0137427 A1 | 6/2011 | Otto et al. | |
| 2011/0137619 A1 | 6/2011 | Otto et al. | |
| 2011/0251694 A1* | 10/2011 | Wasielewski | A61B 19/46 |
| | | | 623/19.11 |
| 2012/0172994 A1* | 7/2012 | Wright | A61F 2/3877 |
| | | | 623/20.18 |
| 2012/0185055 A1* | 7/2012 | Maloney | A61F 2/3859 |
| | | | 623/20.31 |
| 2013/0018477 A1 | 1/2013 | Muratoglu et al. | |
| 2013/0046384 A1 | 2/2013 | Otto et al. | |
| 2014/0228964 A1* | 8/2014 | Lew | A61F 2/3859 |
| | | | 623/20.18 |
| 2014/0364956 A1* | 12/2014 | Jordan | 623/20.33 |
| 2014/0371865 A1* | 12/2014 | Jordan et al. | 623/20.32 |
| 2015/0173909 A1 | 6/2015 | Otto et al. | |

FOREIGN PATENT DOCUMENTS

| | | |
|---|---|---|
| EP | 1374805 A2 | 1/2004 |
| EP | 2731522 A2 | 5/2014 |
| GB | 2252500 A | 8/1992 |
| JP | 11-313845 A | 11/1999 |
| JP | 2004-160179 A | 6/2004 |
| JP | 2005-261538 A | 9/2005 |
| JP | 2010-207652 A | 9/2010 |
| WO | 90/14806 A1 | 12/1990 |
| WO | 2004/058108 A1 | 7/2004 |
| WO | 2005/082039 A2 | 9/2005 |
| WO | 2011/075697 A2 | 6/2011 |
| WO | 2013/009966 A2 | 1/2013 |

OTHER PUBLICATIONS

The extended European search report issued by the European Patent Office on May 29, 2015, which corresponds to European Patent Application No. 12837479.0-1654 and is related to U.S. Appl. No. 14/347,617.

The First Office Action issued by the Chinese Patent Office on Apr. 3, 2015, which corresponds to Chinese Patent Application No. 201280047354.0 and is related to U.S. Appl. No. 14/347,617; with English language translation.

An Office Action; "Notification of Reasons for Refusal," issued by the Japanese Patent Office on Jul. 7, 2015, which corresponds to Japanese Patent Application No. 2011-210410 and is related to U.S. Appl. No. 14/347,617; with English language partial translation.

An Office Action; "Decision of Refusal," issued by the Japanese Patent Office on Feb. 16, 2016, which corresponds to Japanese Patent Application No. 2011-210410 and is related to U.S. Appl. No. 14/347,617; with English language partial translation.

* cited by examiner (a)

(b)

(c)

(a)

(b)

(c)

(a)

(b)

(c)

(a)

(b)

ARTIFICIAL KNEE JOINT IMPLANT

TECHNICAL FIELD

The present invention relates to an artificial knee joint implant for use in surgery for removing an anterior cruciate ligament and a posterior cruciate ligament of a patient, and replacing the knee joint of the patient by an artificial knee joint.

BACKGROUND ART

There is a known artificial knee joint implant including a tibial component fixed to a proximal portion of a tibia and a femoral component fixed to a distal portion of a femur (see Patent Document 1, for example). The femoral component described in Patent Document 1 includes the medial condyle and the lateral condyle arranged side by side in the left-right direction when the femoral component is fixed to the femur. Each of the medial condyle and the lateral condyle includes a distal condyle facing the tibial component at a posture in which the knee is straightened, a posterior condyle disposed posterior to the distal condyle, and a superior condyle disposed superior to the posterior condyle. The distal condyle, the posterior condyle, and the superior condyle form smooth joint surfaces that extend along the periphery of the femoral component so as to be in contact with the surface of the tibial component. Of these, the joint surface on the superior condyle is curved so as to return toward the anterior side of the femoral component. With such a configuration, the femoral component described in Patent Document 1 can be flexed at least by 160 degrees with respect to the tibial component.

CITATION LIST

Patent Document

Patent Document 1: Japanese Patent No. 4290803 (Claims, FIG. 1)

SUMMARY OF INVENTION

Technical Problem

Incidentally, if a posterior stabilized (PS) type artificial knee joint implant is used, an anterior cruciate ligament and a posterior cruciate ligament of a patient are removed. Then, a femoral component having a cam is fixed to a distal portion of a femur of the patient, and a tibial insert having a post is disposed at a proximal portion of a tibia of the patient.

In order to improve the post-operative quality of life (QOL) of a patient to which such a PS-type artificial knee joint implant is attached, it is important to realize more natural flexion state and to increase the maximum flexion angle between the femur and the tibia. That is to say, it is required to realize a stable deep flexion movement in which the femur can be stably flexed at a large flexion angle with respect to the tibia. The inventors of this application focused on the fact that a stable deep flexion movement cannot be realized due to improper balance in gaps (vertical distances) between the femur and the tibia.

The gap balance refers to a balance between an extension gap, which is a gap when the knee is straightened, and a flexion gap, which is a gap when the knee is flexed. If a proper gap balance is achieved, a stable deep flexion movement becomes possible. Conceivable methods for achieving a proper gap balance includes (i) to (v) below.

First, according to the method (i), it is conceivable to peel away (release) as appropriate, from the femur and the tibia, soft tissue around the artificial knee joint, such as the collateral ligament of the patient. However, in this case, the surgeon has to be careful so as not to damage blood vessels and nerves around the soft tissue, and, thus, the operation that installs an artificial knee joint implant requires effort.

Furthermore, according to the method (ii), it is conceivable to change the installation position of the femoral component. Specifically, the femoral component may be installed on the distal portion of the femur, for example, at a position closer to the anterior side or to the posterior side of the femur. However, in this case, a notch may be formed at the distal portion of the femur depending on the shape and the position of a bone resection surface that is formed on the femur in order to fix the femoral component to the femur. If a notch is formed, when an intensive force is applied to the femur, stress is concentrated on the notch, which may cause break in the bone. Furthermore, also when the femoral component is disposed so as to achieve a proper gap balance, the position of the femoral component with respect to the patella may be improper. As a result, a patellar tracking disorder may occur in which the femoral component and the patella cannot smoothly slide over each other.

Furthermore, according to the method (iii), it is conceivable to change the size of the femoral component. More specifically, the size of the femoral component may be made larger or smaller than the originally planned size. However, if the size of the femoral component is increased, the bone resection amount can be small, but a pressure is applied by the large femoral component to the soft tissue, which may make it difficult to flex the knee. On the other hand, if the size of the femoral component is reduced, the bone resection amount of the femur increases. Accordingly, changing the size of the femoral component increases the burden on the patient.

Furthermore, according to the method (iv), it is conceivable to change the thickness of the tibial insert. However, in this case, the height position of a joint line, which is a portion where the tibial insert and the femoral component are in contact with each other, changes. As a result, the above-described patellar tracking disorder and the like may occur.

Furthermore, according to the method (v), it is conceivable to select a femoral component with a posterior condyle having a different thickness, as disclosed in Patent Document 1. However, in this case, flexion (rollback) between the femur and the tibia cannot be made at the original position in the living body depending on the thickness of the posterior condyle, so that the patient may feel a sense of unnaturalness when flexing the knee.

The present invention was made in view of these circumstances, and it is an object thereof to provide an artificial knee joint implant, with which the gap balance can be adjusted in order to realize a stable deep flexion movement, the burden on a surgeon and a patient can be reduced, and the patient can perform a natural flexion movement.

Solution to Problem

In order to achieve the above-described object, a first aspect of the present invention is directed to an artificial knee joint implant for use in surgery for removing an anterior cruciate ligament and a posterior cruciate ligament of a patient, and replacing a knee joint of the patient by an artificial knee joint, including: a femoral component that is to be attached to a distal portion of a femur of the patient; and a tibial insert that is to be attached to a proximal portion of a tibia of the patient. The femoral component includes: a fixing face that is to be fixed to a bone resection surface formed on the distal portion; two femoral joint faces that are curved toward the outer side of the femoral component; a cam portion that is disposed between posterior portions of the two femoral joint faces; posterior condyles that are arranged posterior to the fixing face, and form part of the two femoral joint faces; and superior condyles that are arranged superior to the posterior condyles, and form part of the two femoral joint faces. The tibial insert includes: two tibial joint faces that can slide over the two femoral joint faces; and a post that projects from between the two tibial joint faces to a space between the two femoral joint faces, and can be brought into contact with the cam portion. A plurality of tibial inserts respectively provided with posts having different antero-posterior positions with respect to the tibial joint faces are provided as the tibial insert, and one of the plurality of tibial inserts is to be attached to the proximal portion of the tibia of the patient.

According to this aspect of the present invention, an optimum tibial insert can be selected from among the plurality of tibial inserts and attached to the tibia such that the antero-posterior position of the post is optimum for the patient. Accordingly, the antero-posterior position of the post can be optimized for the patient. If the antero-posterior position of the post is adjusted, the tensile force of the collateral ligament of the patient can be adjusted. As a result, a more proper gap balance can be achieved between an extension gap, which is a gap between the femur and the tibia when the patient's knee is straightened, and a flexion gap, which is a gap between the femur and the tibia when the patient's knee is flexed. Accordingly, a stable deep flexion movement can be realized. Moreover, the post can be disposed as close to the posterior side as possible, while satisfying the condition that the collateral ligament is disposed closer to the anterior side so that the patient can naturally flex the knee. Accordingly, when the cam of the femoral component and the post slide over each other, the flexion angle until the femur or the femoral component impinges on (hits) the tibial insert can be increased. As a result, the deep flexion performance can be improved so that the femur can be flexed at a larger flexion angle with respect to the tibia.

Moreover, contrary to the method (i) described above, it is not necessary to perform the operation that peels away (releases) as appropriate, from the femur and the tibia, soft tissue around the artificial knee joint, such as the collateral ligament of the patient, in order to adjust the gap balance. Thus, it is not necessary to perform the release operation during which the surgeon has to be careful so as not to damage blood vessels and nerves around the soft tissue. Accordingly, the burden on the surgeon and the patient, resulting from the operation that installs an artificial knee joint implant, can be reduced.

Furthermore, contrary to the method (ii) described above, it is not necessary to change the installation position of the femoral component in each case in order to adjust the gap balance. Thus, the degree of freedom in selecting the position where to form the fixing face on the femur can be increased, and, thus, it is not necessary to form a fixing face having a shape that requires the femur to be notched. Accordingly, no stress resulting from the notch is concentrated on the femur, and a decrease in the strength of the femur can be suppressed, and, thus, the burden on the patient can be reduced. Moreover, it is not necessary to change the position of the femoral component in order to adjust the gap balance. Thus, the femoral component can be disposed at a proper position with respect to the patella. As a result, a good sliding state can be achieved between the femoral component and the patella, and the patellar tracking disorder can be suppressed. Accordingly, the patient can naturally flex the knee.

Furthermore, contrary to the method (iii) described above, it is not necessary to change the whole size of the femoral component in order to adjust the gap balance. Thus, it is not necessary to increase or reduce the size of the femoral component in order to adjust the gap balance. Accordingly, the bone resection amount of the femur does not have to be increased, and extra bone resection operation does not have to be performed, and, thus, the burden on the surgeon and the patient can be reduced. Moreover, the problem that a pressure is applied by a large femoral component to soft tissue of the patient can be suppressed, and, thus, the burden on the patient can be reduced.

Furthermore, contrary to the method (iv) described above, it is not necessary to change the thickness of the tibial insert in order to adjust the gap balance. Thus, the height position of a joint line, which is a portion where the tibial insert and the femoral component are in contact with each other, is not affected by the gap balance adjustment. As a result, the relative height position between the femoral component and the patella can be made constant regardless of whether or not the gap balance is adjusted. That is to say, how the femoral component and the patella relatively slide over each other can be made constant regardless of whether or not the gap balance is adjusted. As a result, the above-described patellar tracking disorder and the like can be suppressed.

Furthermore, according to the method (v) described above, a femoral component with a posterior condyle having a different thickness is selected in order to adjust the gap. According to this method, the balance of the relative positions between the collateral ligament and the femoral component cannot be adjusted. On the other hand, according to the first aspect of the present invention, the relative positions between the collateral ligament and the femoral component can be adjusted by adjusting the antero-posterior position of the post of the tibial insert. As a result, the femur can be flexed with respect to the tibia at a position close to the original position in the living body, and, thus, the patient's knee can be flexed at a natural posture.

Accordingly, the present invention can provide an artificial knee joint implant, with which the gap balance can be adjusted in order to realize a stable deep flexion movement, the burden on a surgeon and a patient can be reduced, and the patient can perform a natural flexion movement.

A second aspect of the present invention is directed to the artificial knee joint implant according to the first aspect, wherein a plurality of femoral components respectively provided with fixing faces having the same shape and posterior condyles having different thicknesses are provided as the femoral component, and one of the plurality of femoral components is to be attached to the distal portion of the femur of the patient.

According to this aspect of the present invention, an optimum femoral component is selected from among the plurality of femoral components such that a proper gap balance can be achieved between the femur and the tibia, and, at the same time, the collateral ligament can be disposed so as to realize natural flexion of the knee. For example, if the patient has a small flexion gap, the gap balance can be adjusted by using a femoral component with a posterior condyle having a smaller thickness. Furthermore, if the patient has a large flexion gap, the gap balance can be adjusted by using a femoral component with a posterior condyle having a larger thickness. Furthermore, in order to arrange the position of the collateral ligament closer to the anterior side when the knee is flexed, it is preferable that a femoral component with a posterior condyle having a smaller thickness is selected to use from among the femoral components. Moreover, the range in which the gap balance can be adjusted can be increased, and the gap balance can be finely controlled, by combining the femoral component with one of the tibial inserts with posts having different antero-posterior positions. Moreover, the arrangement of the collateral ligament can be more easily adjusted, and a better state can be provided for the user, by combining femoral components with posterior condyles having different thicknesses and tibial inserts with posts having different antero-posterior positions. Accordingly, a femoral component with a posterior condyle having an optimum thickness can be used such that a proper gap balance can be achieved, and, at the same time, the arrangement of the collateral ligament can be optimized.

A third aspect of the present invention is directed to the artificial knee joint implant according to the second aspect, wherein the femoral joint faces on the posterior condyles respectively in the plurality of femoral components have different radii of curvature.

According to this aspect of the present invention, with a simple configuration causing the femoral joint faces on the posterior condyles respectively in the femoral components to have different radii of curvature, the posterior condyles of the femoral components can have different thicknesses.

A fourth aspect of the present invention is directed to the artificial knee joint implant according to any one of the first to the third aspects, wherein the plurality of posts have the same shape.

According to this aspect of the present invention, the posts of the plurality of tibial inserts have the same shape. Thus, during surgery for installing the artificial knee joint, the movement of the femur with respect to the tibia when changing the type of tibial insert can be easily predicted. Thus, the surgeon can easily select an optimum tibial insert for the patient. As a result, the duration of surgery can be shortened, and, thus, the burden on the surgeon and the patient can be further reduced.

A fifth aspect of the present invention is directed to the artificial knee joint implant according to any one of the first to the fourth aspects, further including a tibial tray that is to be fixed to the proximal portion of the tibia, supports the tibial insert, and constitutes a tibial component in cooperation with the tibial insert; wherein the tibial tray is formed in one piece with the tibial insert, or is formed as a member independent of the tibial insert and is fixed to the tibial insert.

According to this aspect of the present invention, the tibial tray can be used to fix the tibial insert to the proximal portion of the tibia. Furthermore, a stable deep flexion movement between the femur and the tibia is realized by changing the antero-posterior position of the post of the tibial insert. Accordingly, it is not necessary to change the shape of the tibial tray in order to realize a stable deep flexion movement. Thus, it is not necessary to change the shape of the proximal portion of the tibia to which the tibial tray is to be fixed, in order to realize a stable deep flexion movement. Accordingly, the burden on the surgeon and the patient can be reduced.

Advantageous Effects of Invention

The present invention can provide an artificial knee joint implant, with which the gap balance can be adjusted in order to realize a stable deep flexion movement, the burden on a surgeon and a patient can be reduced, and the patient can perform a natural flexion movement.

DESCRIPTION OF EMBODIMENTS

Hereinafter, an embodiment for carrying out the present invention will be described with reference to the drawings. The present invention is widely applicable as an artificial knee joint implant for use in surgery for replacing the knee joint by an artificial knee joint.

Figure 1:
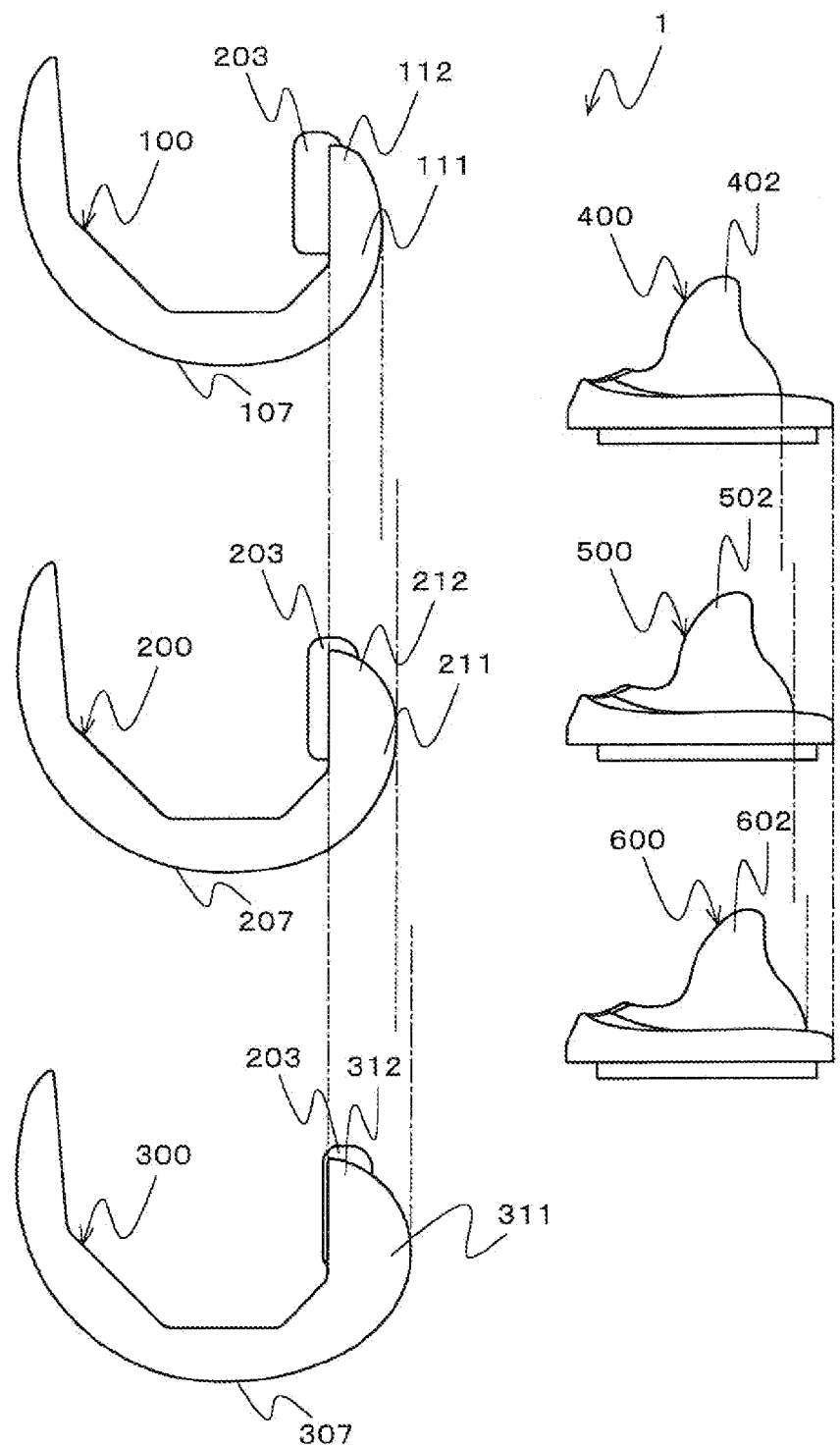
FIG. 1 is a side view of an artificial knee joint implant according to an embodiment of the present invention.

FIG. 1 is a side view of an artificial knee joint implant 1 according to an embodiment of the present invention. The artificial knee joint implant 1 can be used in surgery for replacing the knee joint of a patient by an artificial knee joint. The artificial knee joint implant 1 is used, for example, to recover normal functions of the patient's knee in which the knee joint has been highly deformed due to osteoarthritis, chronic rheumatoid arthritis, or the like.

The artificial knee joint implant 1 includes a plurality of femoral components 100, 200, and 300 and a plurality of tibial inserts 400, 500, and 600. When carrying out PS-type artificial knee joint replacement surgery for removing an anterior cruciate ligament and a posterior cruciate ligament of a patient, and replacing the knee joint of the patient by an artificial knee joint, the surgeon selects one femoral component from among the plurality of femoral components 100, 200, and 300 of the artificial knee joint implant 1. Furthermore, when carrying out surgery, the surgeon selects one tibial insert from among the plurality of tibial inserts 400, 500, and 600. Accordingly, during surgery, a femoral component and a tibial component that are optimum for the patient are selected from among the plurality of femoral components 100, 200, and 300 and tibial inserts 400, 500, and 600.

Note that the plurality of femoral components 100, 200, and 300 have substantially similar configurations except that their posterior condyles 111, 211, and 311 have different thicknesses. Furthermore, the plurality of tibial inserts 400, 500, and 600 have substantially similar configurations except that their posts 402, 502, and 602 have different antero-posterior positions. Hereinafter, the configuration of one femoral component 200 of the plurality of femoral components 100, 200, and 300 will be mainly described. Furthermore, the configuration of one tibial insert 500 of the plurality of tibial inserts 400, 500, and 600 will be mainly described.

Figure 2:
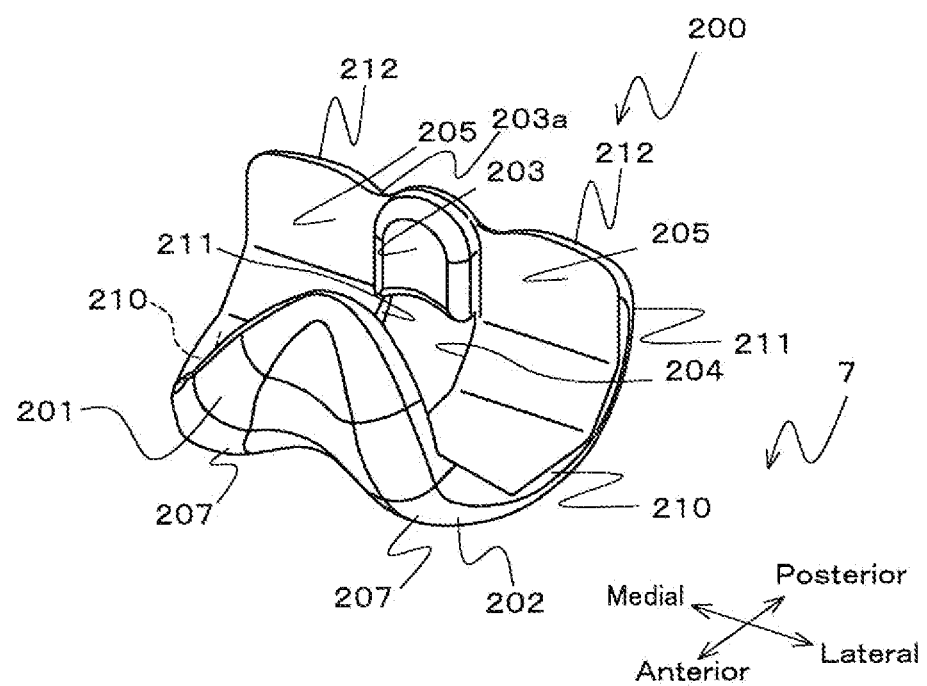
FIG. 2 is a perspective view of a femoral component and a tibial insert.
Figure 2:
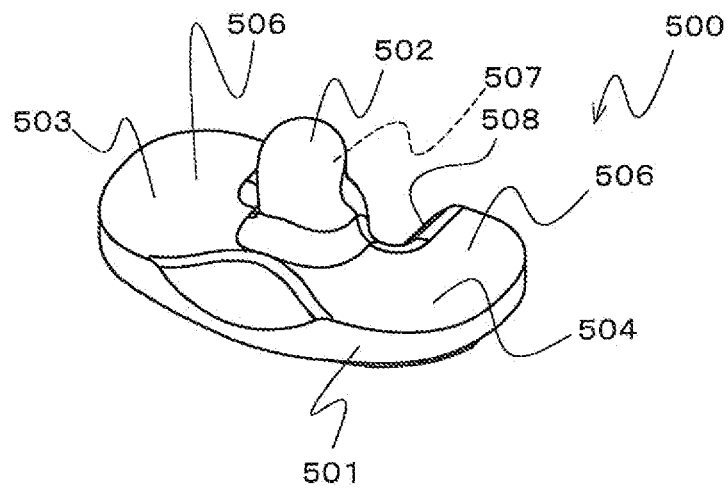
Figure 3:
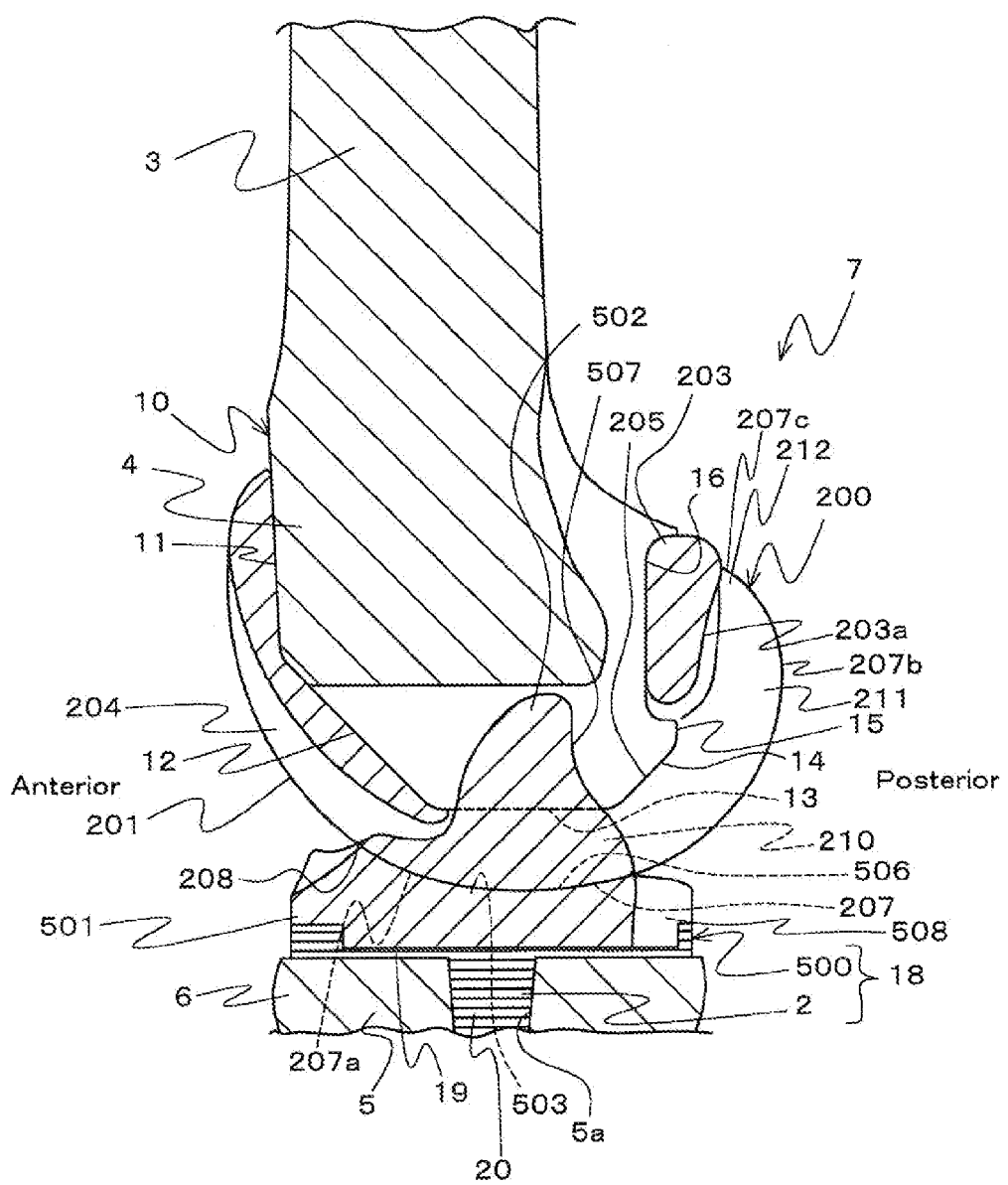
FIG. 3 is a cross-sectional view showing the state in which the femoral component is fixed to the femur of the patient and the tibial component is fixed to the tibia of the patient, viewed from a side of the patient.

FIG. 2 is a perspective view of the femoral component 200 and the tibial insert 500. FIG. 3 is a cross-sectional view showing the state in which the femoral component 200 is attached to a distal portion 4 of a femur 3 of the patient and the tibial insert 500 is attached to a proximal portion 6 of a tibia 5 of the patient, viewed from a side of the patient. As shown in FIGS. 2 and 3, the femoral component 200 is fixed to the distal portion 4 of the femur 3. Furthermore, the tibial insert 500 is fixed via a tibial tray 2 to the proximal portion 6 of the tibia 5. The femoral component 200 and the tibial insert 500 relatively slide over each other as the patient's knee is flexed and extended. The femoral component 200, the tibial insert 500, and the tibial tray 2 form an artificial knee joint 7.

In the description below, "medial" and "lateral" respectively refer to the inner side and the outer side with respect to the midline of the body, of the patient's knee on which the femoral component 200 and the tibial insert 500 are installed. That is to say, if the femoral component 200 and the tibial insert 500 are arranged on the left leg of the patient, the medial side refers to the right side of the patient, and the lateral side refers to the left side of the patient. Furthermore, "anterior" and "posterior" respectively refer to the front side and the back side of the patient.

The femoral component 200 is made of, for example, a metal material having vital affinity. The femoral component 200 is in the shape of a U when viewed from a side. The femoral component 200 is configured including a medial condyle 201, a lateral condyle 202, a cam portion 203, and an opening portion 204. The medial condyle 201 and the lateral condyle 202 are arranged side by side in the left-right direction. The anterior portion of the medial condyle 201 and the anterior portion of the lateral condyle 202 are connected to each other. The anterior portion of the femoral component 200 projects to the superior side when viewed from the front.

The medial condyle 201 and the lateral condyle 202 are provided with, on inner faces thereof facing the distal portion 4 of the femur 3, fixing faces 205. The fixing faces 205 are provided in order to fix the femoral component 200 to the distral portion 4 of the femur 3. Furthermore, each of the fixing faces 205 is in the shape of a U when viewed from a side. The fixing faces 205 are fixed to a bone resection surface 10 formed on the distal portion 4.

The bone resection surface 10 is a face artificially formed by a surgeon before fixing the femoral component 200 to the distal portion 4. The bone resection surface 10 is formed, for example, by the surgeon removing part of the distal portion 4 using a tool such as a cutter. The bone resection surface 10 has, for example, a first face 11 oriented to the anterior side, a second face 12 obliquely oriented to the anterior and inferior side, a third face 13 oriented to the inferior side, a fourth face 14 obliquely oriented to the posterior and inferior side, and a fifth face 15 oriented to the posterior side. Each of the fixing faces 205 is formed in the shape along the first to the fifth faces 11 to 15, and is fixed to the first to the fifth faces 11 to 15 using bone cement, bioactive material coating, or the like.

Furthermore, the bone resection surface 10 is provided with a recess portion 16 in which a post 502 (described later) is to be disposed over the area from the second face 12 to the fifth face 15. The recess portion 16 is formed extending from the second face 12 to the fifth face 15, and extends in the antero-posterior direction. The recess portion 16 extends through the distal portion 4 in the antero-posterior direction. Accordingly, the recess portion 16 prevents the post 502 from coming in contact with the femur 3 when the knee is flexed.

The medial condyle 201 and the lateral condyle 202 are provided with, on outer faces thereof facing the side opposite from the distal portion 4 of the femur 3, two femoral joint faces 207. The femoral joint faces 207 are provided as curved faces that slide over the tibial insert 500 as the patient's knee is flexed and extended. Each of the femoral joint faces 207 is in the shape of a projecting curve, is opposite from the third face 13, which is the distal end of the distal portion 4, and is opposite from the fifth face 15, which is the posterior portion of the distal portion 4, so that the femoral joint faces 207 surround part of the distal portion 4 when viewed from a side. An anterior end 208 of the femoral joint face 207 is disposed anterior to the post 502 when the knee is straightened.

The femoral joint faces 207 are configured by distal condyles 210, posterior condyles 211, and superior condyles 212 included in the medial condyle 201 and the lateral condyle 202.

Figure 4:
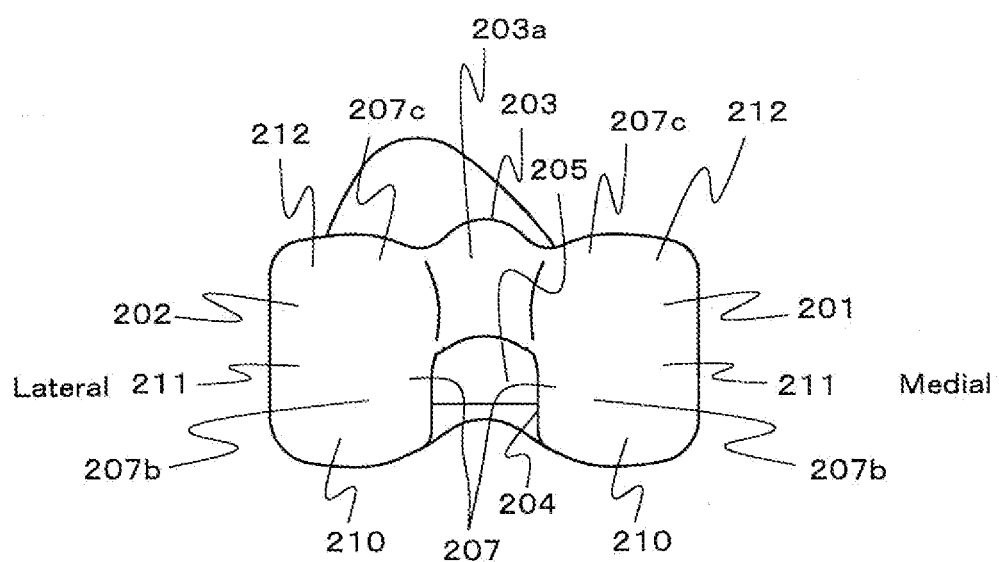
FIG. 4 is a rear view of the femoral component.

FIG. 4 is a rear view of the femoral component 200. As shown in FIGS. 3 and 4, the distal condyles 210 are arranged opposing the third face 13, which is the distal face of the distal portion 4 of the femur 3. The posterior condyles 211 are provided as portions obliquely extending to the posterior and superior side from the distal condyles 210. The posterior condyles 211 are arranged posterior to the fixing faces 205, and are arranged opposing mainly the fourth face 14 and the fifth face 15. The superior ends of the posterior condyles 211 are positioned posterior to the cam portion 203 when viewed from a side. The superior condyles 212 are provided as portions extending to the superior side from the superior ends of the posterior condyles 211. The superior condyles 212 are arranged opposing the fifth face 15.

According to the above-described configuration, the femoral joint faces 207 respectively have first joint faces 207a, which are the outer faces of the distal condyles 210, second joint faces 207b, which are the outer faces of the posterior condyles 211, and third joint faces 207c, which are the outer faces of the superior condyles 212.

The cam portion 203 is disposed between the medial condyle 201 and the lateral condyle 202. The cam portion 203 is disposed between the posterior portions of the femoral joint faces 207. When the flexion angle of the knee is a predetermined angle or more, the cam portion 203 is brought into contact with the tibial insert 500, thereby guiding the flexion movement of the knee. The cam portion 203 is a portion made of a small piece disposed between the posterior condyle 211 and the superior condyle 212 of the medial condyle 201 and the posterior condyle 211 and the superior condyle 212 of the lateral condyle 202.

As shown in FIGS. 2 and 3, the anterior portion of the cam portion 203 projects to the anterior side with respect to the fixing faces 205. The anterior face of the cam portion 203 is formed as a flat face. Furthermore, the posterior face of the cam portion 203 is disposed anterior to the outer faces (the third joint faces 207c) of the superior condyles 212. Accordingly, the posterior portion of the cam portion 203 is provided with a depression 203a that is depressed to the anterior side. The opening portion 204 is formed anterior to the cam portion 203.

The opening portion 204 is a portion through which the post 502 of the tibial insert 500 is inserted. The opening portion 204 is disposed between the medial condyle 201 and the lateral condyle 202, and is provided as an opening that is formed through the femoral component 200. The opening portion 204 extends to the anterior side from the posterior condyles 211 of the medial condyle 201 and the lateral condyle 202.

The thus configured femoral component 200 is slidably supported by a tibial component 18. The tibial component 18 is configured including the tibial tray 2 and the tibial insert 500 as constituent components of the artificial knee joint implant 1. The tibial tray 2 is configured including a tray main body 19 that supports the tibial insert 500, and a stud portion 20 that projects from the bottom face of the tray main body 19. The stud portion 20 is fitted into a medullary cavity portion 5a that is formed in the proximal portion 6 of the tibia 5, and is fixed to the proximal portion 6 of the tibia 5 using bone cement, bioactive material coating, or the like. The medullary cavity portion 5a is an opening formed by the surgeon. The tray main body 19 is in the shape of a flat plate, and is disposed on the end face of the proximal portion 6. The tray main body 19 has a surface facing the femoral component 200. The tibial insert 500 is fixed to this surface of the tray main body 19.

The tibial insert 500 is made of synthetic resin or the like, and is configured including a flat plate 501, and a post 502 that projects from the plate 501 into the opening portion 204. The plate 501 is in the shape of a disk that is elongated in the left-right direction. The plate 501 is provided with a medial recess 503 and a lateral recess 504.

The medial recess 503 and the lateral recess 504 are provided as depressions that are in slidable contact respectively with the medial condyle 201 and the lateral condyle 202 of the femoral component 200. The post 502 is disposed between the medial recess 503 and the lateral recess 504. The medial recess 503 and the lateral recess 504 are arranged on both sides of the post 502 when viewed from above. In each of the medial recess 503 and the lateral recess 504, the anterior end is thicker than the posterior end. The medial recess 503 and the lateral recess 504 have depressions that respectively receive the medial condyle 201 and the lateral condyle 202 of the femoral component 200.

A tibial joint face 506 is formed on a face of the medial recess 503 opposing the medial condyle 201 of the femoral component 200. In a similar manner, a tibial joint face 506 is formed on a face of the lateral recess 504 opposing the lateral condyle 202 of the femoral component 200. Each of the two tibial joint faces 506 is in the shape of a curve recessed toward the proximal portion 6 of the tibia 5. The tibial joint face 506 of the medial recess 503 is in slidable contact with the femoral joint face 207 of the medial condyle 201. Furthermore, the tibial joint face 506 of the lateral recess 504 is in slidable contact with the femoral joint face 207 of the lateral condyle 202.

The post 502 is provided in order to facilitate flexion of the artificial knee joint 7, by sliding over the cam portion 203. The post 502 is disposed substantially at the center of the plate 501 when the plate 501 is viewed from above. That is to say, the post 502 is disposed at the center of the plate 501 in the left-right direction, and is disposed at the center of the plate 501 in the antero-posterior direction.

The post 502 is in the shape of a column having a thickness in the antero-posterior direction that is reduced as the height from the plate 501 increases. Furthermore, when the post 502 is viewed from the front, the post 502 has a thickness in the left-right direction that is constant from the root to the middle, and then is gradually reduced such that the tip of the post 502 is in a tapered shape.

The posterior face of the post 502 is provided with a sliding face 507 that is to be brought into contact with and slide over the cam portion 203. The sliding face 507 is provided as a face that is depressed toward the anterior side, and slides over the cam portion 203 when the flexion angle of the artificial knee joint 7 is a predetermined value or more.

A cut-out portion 508 is formed posterior to the post 502 of the plate 501. The cut-out portion 508 is provided in order to prevent the cam portion 203 from coming in contact with the plate 501 when the cam portion 203 is in contact with the post 502. The cut-out portion 508 is formed at the center in the left-right direction of the posterior end of the plate 501.

Figure 5:
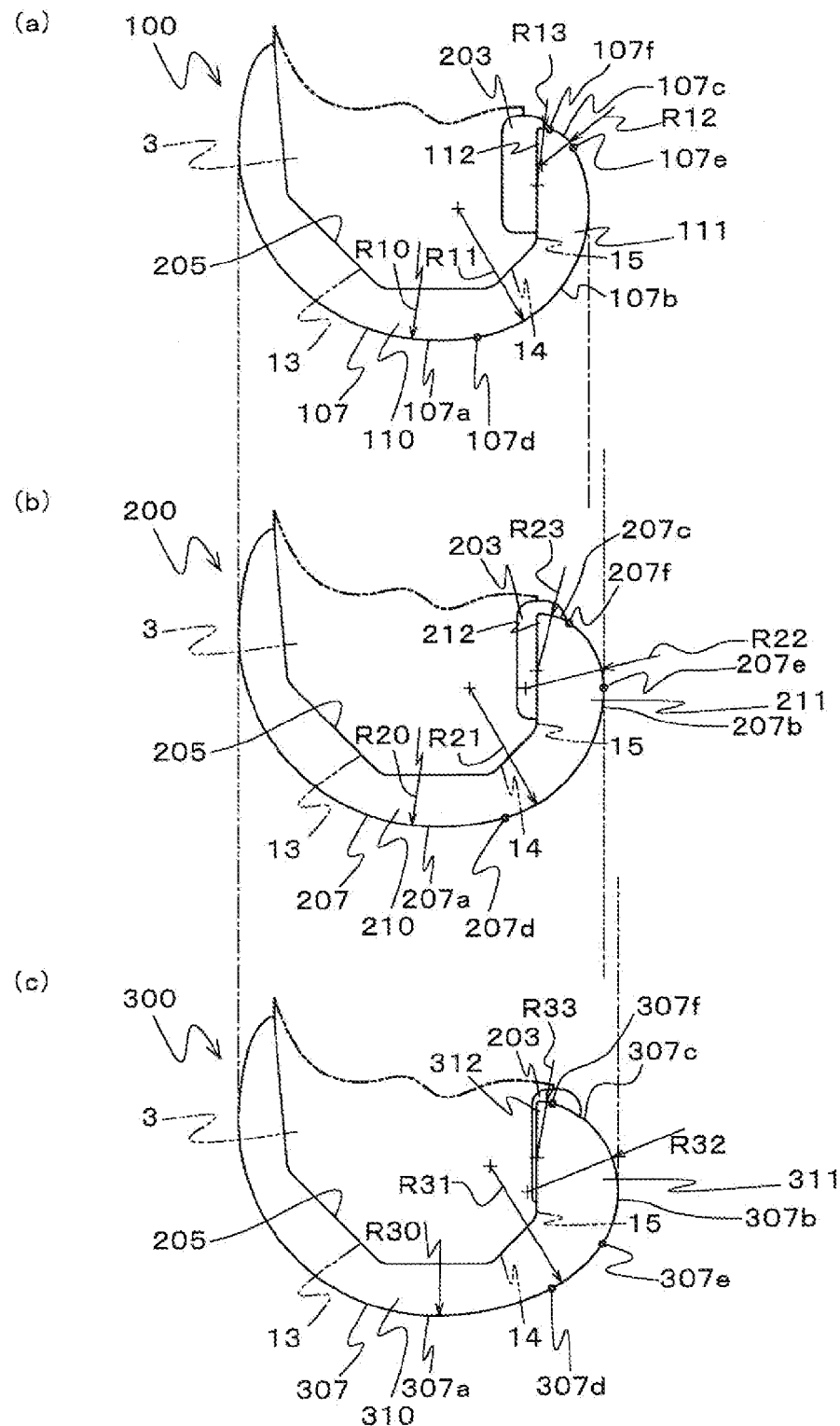
FIGS. 5(a), 5(b), and 5(c) are respectively side views of a plurality of femoral components.

FIGS. 5(a), 5(b), and 5(c) are respectively side views of the plurality of femoral components 100, 200, and 300. As shown in FIG. 5(b), the femoral joint face 207 of the femoral component 200 has a plurality of radii of curvature. Specifically, the femoral joint face 207 has radii of curvature R20, R21, R22, and R23.

The femoral joint face 207 has, on an anterior portion in the distal condyle 210, the radius of curvature R20. A posterior end 207d of the portion in the femoral joint face 207 having the radius of curvature R20 is positioned inferior to the fourth face 14 of the femur 3. The femoral joint face 207 has, on a portion extending to the posterior side from the posterior end 207d, the radius of curvature R21 that is smaller than the radius of curvature R20. The portion in the femoral joint face 207 having the radius of curvature R21 extends to the posterior end of the femoral component 200. A posterior end 207e of the portion in the femoral joint face 207 having the radius of curvature R21 is positioned posterior to the cam portion 203. The femoral joint face 207 has, on a portion extending from the posterior end 207e toward the fixing face 205, the radius of curvature R22 that is smaller than the radius of curvature R21. An anterior end 207f of the portion in the femoral joint face 207 having the radius of curvature R22 is positioned close to the superior portion of the cam portion 203 when viewed from a side. The femoral joint face 207 has, on a portion extending from the anterior end 207f to the fixing face 205, the radius of curvature R23 that is smaller than the radius of curvature R22. That is to say, R20>R21>R22>R23.

According to the above-described configuration, the femoral joint face 207 (the first joint faces 207a) of the distal condyle 210 has two radii of curvature R20 and R21. The femoral joint face 207 (the second joint faces 207b) of the posterior condyle 211 has two radii of curvature R21 and R22. The femoral joint face 207 (the third joint faces 207c) of the superior condyle 212 has two radii of curvature R22 and R23.

Next, the femoral component 100 and the femoral component 300 will be described with reference to FIGS. 5(a), 5(b), and 5(c). As described above, the femoral components 100, 200, and 300 differ from each other mainly in the thicknesses of the posterior condyles 111, 211, and 311 when viewed from a side. It should be noted that constituent components of the femoral component 100 and 300 similar to those of the femoral component 200 are denoted by the same reference numerals as those of the femoral component 200 in the drawings, and a description thereof has been omitted. Furthermore, constituent components of the femoral component 100 and 300 corresponding to those of the femoral component 200 will be described using reference numerals corresponding to those of the femoral component 200. For example, the femoral joint faces of the femoral component 100 and 300 are denoted by 107 and 307, which are reference numerals corresponding to 207 denoting the femoral joint face of the femoral component 200.

As shown in FIG. 5(a), the femoral component 100 has a distal condyle 110, a posterior condyle 111, and a superior condyle 112. Furthermore, the femoral joint face 107 of the femoral component 100 has a plurality of radii of curvature. Specifically, the femoral joint face 107 has radii of curvature R10, R11, R12, and R13.

The femoral joint face 107 has, on an anterior portion in the distal condyle 110, the radius of curvature R10. A posterior end 107d of the portion in the femoral joint face 107 having the radius of curvature R10 is positioned inferior to the third face 13 of the femur 3. The femoral joint face 107 has, on a portion extending to the posterior side from the posterior end 107d, the radius of curvature R11 that is smaller than the radius of curvature R10. The portion in the femoral joint face 107 having the radius of curvature R11 includes the posterior end of the femoral component 100, and extends to the superior side from the posterior end. A superior end 107e of the portion having the radius of curvature R11 is positioned posterior to the superior portion of the cam portion 203. The femoral joint face 107 has, on a portion extending from the superior end 107e toward the fixing face 205, the radius of curvature R12 that is smaller than the radius of curvature R11. An anterior end 107f of the portion in the femoral joint face 107 having the radius of curvature R12 overlaps the cam portion 203 when viewed from a side. The femoral joint face 107 has, on a portion extending from the anterior end 107f to the fixing face 205, the radius of curvature R13 that is smaller than the radius of curvature R12. That is to say, R10>R11>R12>R13.

According to the above-described configuration, the femoral joint face 107 (a first joint face 107a) of the distal condyle 110 has two radii of curvature R10 and R11. The femoral joint face 107 (a second joint face 107b) of the posterior condyle 111 has one radius of curvature R11. The femoral joint face 107 (a third joint face 107c) of the superior condyle 112 has two radii of curvature R12 and R13.

As shown in FIG. 5(c), the femoral component 300 has a distal condyle 310, a posterior condyle 311, and a superior condyle 312. Furthermore, the femoral joint face 307 of the femoral component 300 has a plurality of radii of curvature. Specifically, the femoral joint face 307 has radii of curvature R30, R31, R32, and R33.

The femoral joint face 307 has, on an anterior portion in the distal condyle 310, the radius of curvature R30. A posterior end 307d of the portion in the femoral joint face 307 having the radius of curvature R30 is positioned posterior to the fixing face 205. The femoral joint face 307 has, on a portion extending to the posterior side from the posterior end 307d, the radius of curvature R31 that is smaller than the radius of curvature R30. The portion in the femoral joint face 307 having the radius of curvature R31 obliquely projects to the posterior and inferior side. A posterior end 307e of the portion in the femoral joint face 307 having the radius of curvature R31 is positioned, in the antero-posterior direction, between the fixing face 205 and the posterior end of the femoral component 300. The femoral joint face 307 has, on a portion extending to the superior side from the posterior end 307e, the radius of curvature R32 that is smaller than the radius of curvature R31. The portion in the femoral joint face 307 having the radius of curvature R32 includes the posterior end of the femoral component 300, and extends to the superior side from the posterior end. A superior end 307f of the portion having the radius of curvature R32 is positioned overlapping the cam portion 203 when viewed from a side. The femoral joint face 307 has, on a portion extending from the superior end 307f to the fixing face 205, the radius of curvature R33 that is smaller than the radius of curvature R32. That is to say, R30>R31>R32>R33.

According to the above-described configuration, the femoral joint face 307 (a first joint face 307a) of the distal condyle 310 has at least one radius of curvature R31. The femoral joint face 307 (a second joint face 307b) of the posterior condyle 311 has two radii of curvature R31 and R32. The femoral joint face 307 (a third joint face 307c) of the superior condyle 312 has two radii of curvature R32 and R33. The fixing faces 205 of the thus configured femoral components 100, 200, and 300 have the same shape. Furthermore, the radii of curvature are such that R10=R20=R30, and the wall thicknesses of the distal condyles 110, 210, and 310 positioned inferior to the third face 13 are substantially the same.

Meanwhile, the radii of curvature are such that R11<R21<R31. Furthermore, R12<R22<R32, and R13<R23<R33. With such a configuration providing different radii of curvature, the posterior condyle 211 of the femoral component 200 is thicker than the posterior condyle 111 of the femoral component 100, and the posterior condyle 311 of the femoral component 300 is thicker than the posterior condyle 211 of the femoral component 200.

Figure 6:
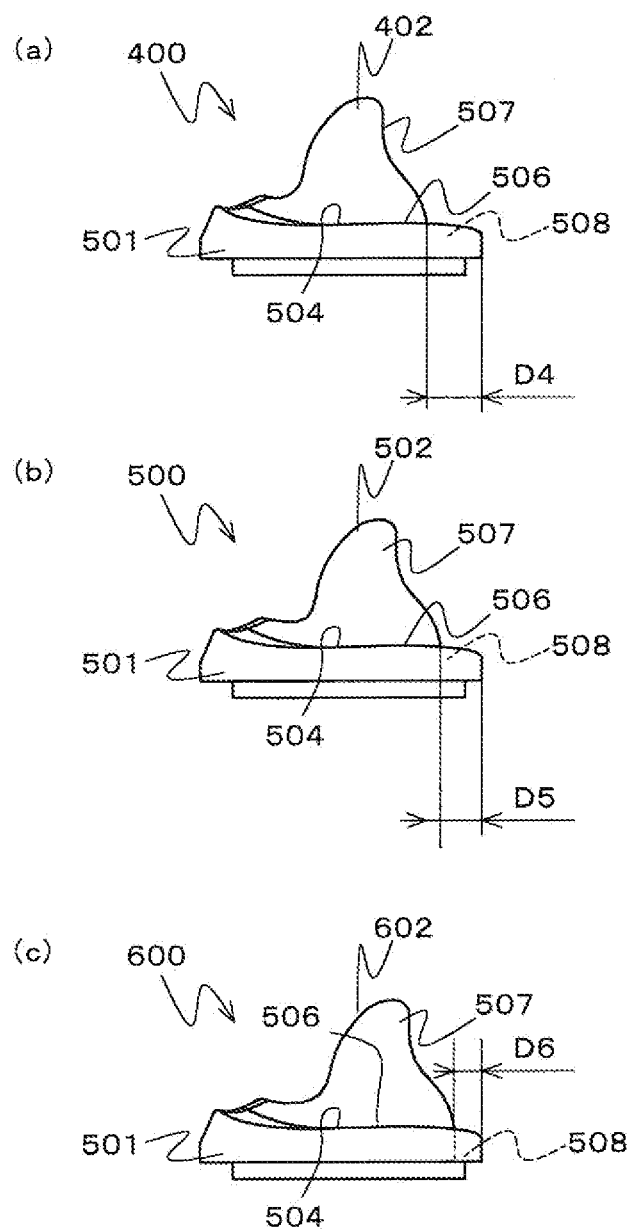
FIGS. 6(a), 6(b), and 6(c) are respectively side views of tibial inserts.

FIGS. 6(a), 6(b), and 6(c) are respectively side views of the plurality of tibial inserts 400, 500, and 600. Next, the tibial insert 500 and the tibial insert 600 will be described with reference to FIGS. 6(a), 6(b), and 6(c). As described above, the tibial inserts 400, 500, and 600 differ from each other mainly in the antero-posterior positions of the posts 402, 502, and 602. It should be noted that constituent components of the tibial inserts 400 and 600 similar to those of the tibial insert 500 are denoted by the same reference numerals as those of the tibial insert 500 in the drawings, and a description thereof has been omitted.

The posts 402, 502, and 602 of the tibial inserts 400, 500, and 600 have the same shape. On the other hand, the posts 402, 502, and 602 have different antero-posterior positions with respect to the tibial joint face 506. Specifically, in the tibial insert 400, the distance in the antero-posterior direction from the posterior end of the plate 501 to the posterior end of the post 402 is defined as a distance D4. In the tibial insert 500, the distance in the antero-posterior direction from the posterior end of the plate 501 to the posterior end of the post 502 is defined as a distance D5. In the tibial insert 600, the distance in the antero-posterior direction from the posterior end of the plate 501 to the posterior end of the post 602 is defined as a distance D6. In this case, the distances are such that D4>D5>D6. Accordingly, the cutting depth to the anterior side of the cut-out portion 508 from the posterior end of the plate 501 varies between the tibial inserts 400, 500, and 600 in a similar manner.

Description of Flexion Movement of the Artificial Knee Joint

FIGS. 7(a), 7(b), and 7(c) are respectively cross-sectional views for illustrating a flexion movement of the artificial knee joint 7, showing the main portion viewed from a side, in a state where the flexion angle of the artificial knee joint 7 is zero. FIGS. 7(a), 7(b), and 7(c) each show the case in which the artificial knee joint 7 includes a different tibial insert. More specifically, FIG. 7(a) shows the case in which the artificial knee joint 7 includes the tibial insert 400, FIG. 7(b) shows the case in which the artificial knee joint 7 includes the tibial insert 500, and FIG. 7(c) shows the case in which the artificial knee joint 7 includes the tibial insert 600.

Figure 7:
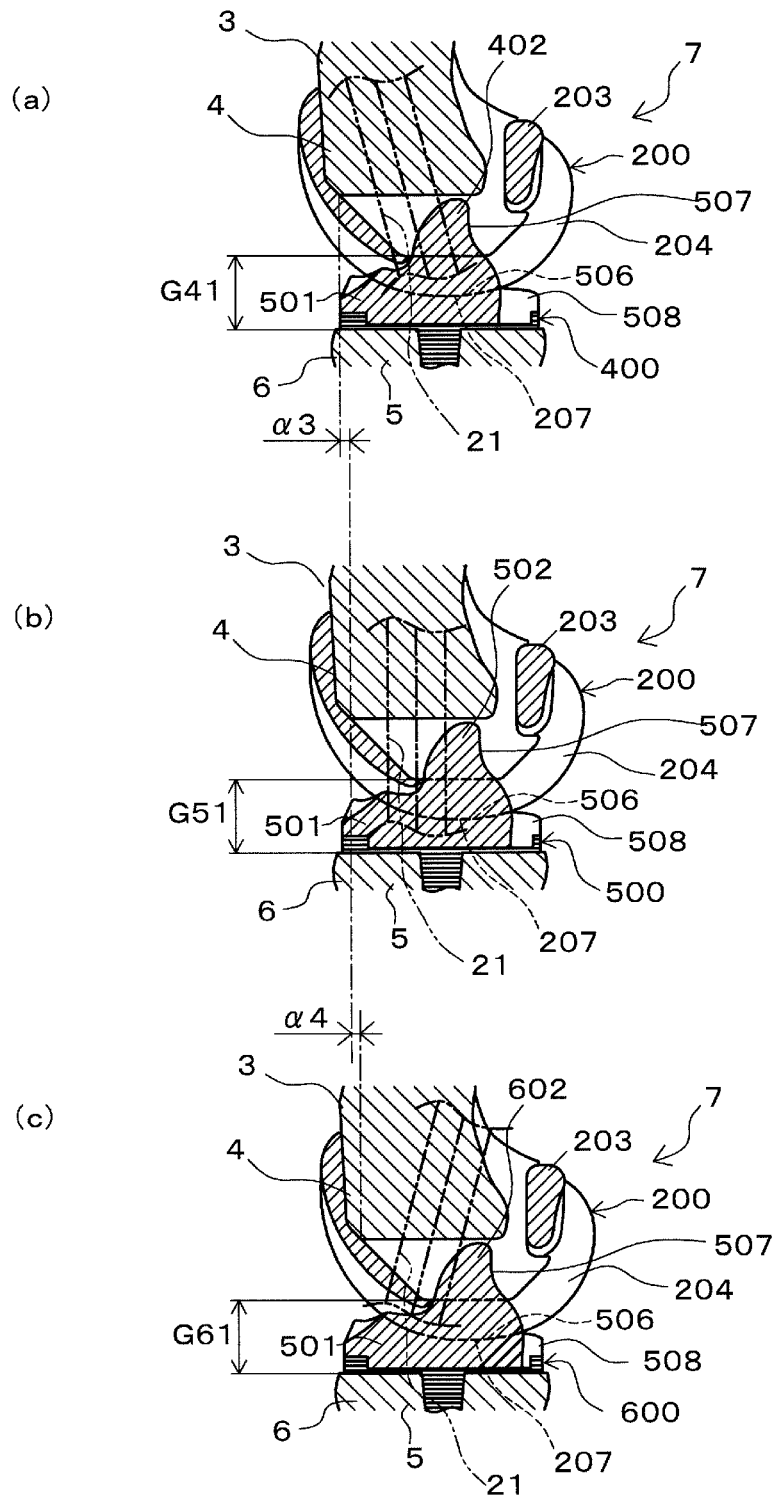
FIGS. 7(a), 7(b), and 7(c) are respectively cross-sectional views for illustrating a flexion movement of the artificial knee joint, showing the main portion viewed from a side, in a state where the flexion angle of the artificial knee joint is zero.
Figure 8:
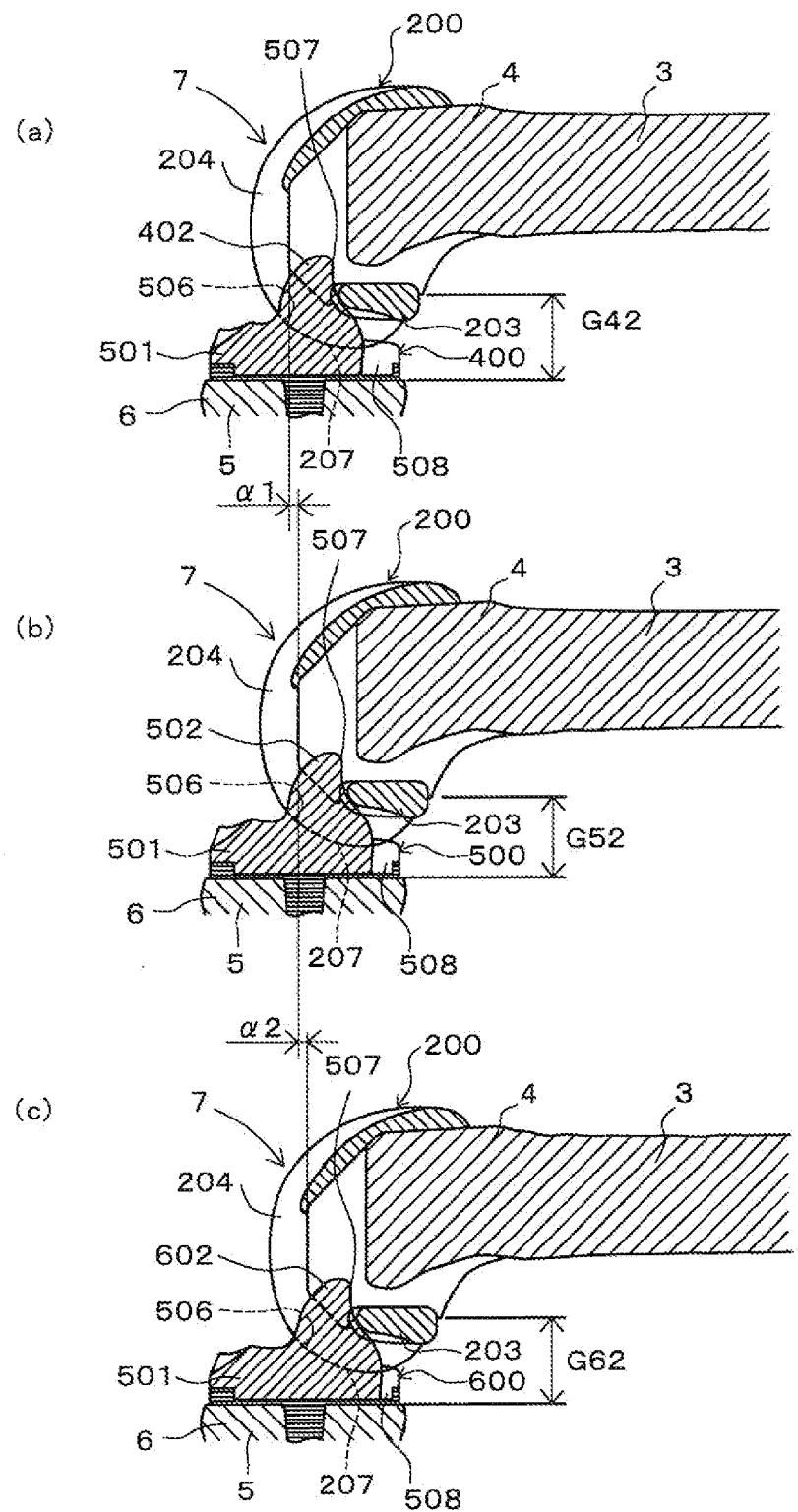
FIGS. 8(a), 8(b), and 8(c) are respectively cross-sectional views for illustrating a flexion movement of the artificial knee joint, showing the main portion viewed from a side, in a state where the flexion angle of the artificial knee joint is 90 degrees.

Furthermore, FIGS. 8(a), 8(b), and 8(c) are respectively cross-sectional views for illustrating a flexion movement of the artificial knee joint 7, showing the main portion viewed from a side, in a state where the flexion angle of the artificial knee joint 7 is 90 degrees. FIGS. 8(a), 8(b), and 8(c) are views respectively corresponding to FIGS. 7(a), 7(b), and 7(c).

FIGS. 7(a) and 8(a) show a flexion movement of the artificial knee joint 7 in the case of using the tibial insert 400. FIGS. 7(b) and 8(b) show a flexion movement of the artificial knee joint 7 in the case of using the tibial insert 500. FIGS. 7(c) and 8(c) show a flexion movement of the artificial knee joint 7 in the case of using the tibial insert 600.

As shown in FIG. 7(b), in the case where the artificial knee joint 7 is configured including the tibial insert 500, when flexion of the artificial knee joint 7 is started, the femoral joint face 207 of the femoral component 200 pivots to the anterior side while sliding over the tibial joint face 506. At that time, the femur 3 and the femoral component 200 rotate clockwise in FIG. 7(b). Accordingly, the cam portion 203 of the femoral component 200 moves to the anterior side, and the cam portion 203 is displaced so as to approach the post 502.

Then, when the flexion angle increases to be the predetermined angle or more, as shown in FIG. 8(b), the cam portion 203 of the femoral component 200 is brought into contact with the sliding face 507 of the post 502. Accordingly, when the artificial knee joint 7 is flexed, the cam portion 203 is received by the sliding face 507 of the post 502, and slidingly rotates over the sliding face 507 while its displacement to the anterior side is being restricted. Accordingly, the femoral component 200 further rotates using, as a fulcrum, the contact portion with the post 502.

It should be noted that, as shown in FIGS. 7(a) and 8(a), also in the case where the artificial knee joint 7 is configured including the tibial insert 400, a flexion movement similar to that in the case of using the tibial insert 500 is performed. Furthermore, as shown in FIGS. 7(c) and 8(c), also in the case where the artificial knee joint 7 is configured including the tibial insert 600, a flexion movement similar to that in the case of using the tibial insert 500 is performed. Furthermore, also in the case where the femoral component 100 or the femoral component 300 (see FIG. 5) is used instead of the femoral component 200, a flexion movement similar to that described above is performed.

Adjustment of the Gap Balance by Changing the Tibial Component

Referring to FIGS. 7(b) and 8(b), in an extension state, which is a state where the flexion angle of the artificial knee joint 7 is zero, the distance between the distal portion 4 of the femur 3 and the proximal portion 6 of the tibia 5 is a predetermined extension gap G51. Furthermore, in a state where the flexion angle of the artificial knee joint 7 is 90 degrees, the distance between the distal portion 4 of the femur 3 and the proximal portion 6 of the tibia 5 is a predetermined flexion gap G52. The gap between the extension gap G51 and the flexion gap G52 is defined as a gap balance. It should be noted that a gap refers to a distance in a straight line between the distal portion 4 of the femur 3 and the proximal portion 6 of the tibia 5, taken along the central axis of the tibia 5. An extension gap refers to a gap when the artificial knee joint 7 is straightened such that the flexion angle is zero. A flexion gap refers to a gap when the artificial knee joint 7 is flexed such that the flexion angle is 90 degrees.

Furthermore, as shown in FIGS. 7(a) and 8(a), an extension gap G41 and a flexion gap G42 of the artificial knee joint 7 configured including the tibial insert 400 are defined. The gap between the extension gap G41 and the flexion gap G42 is defined as a gap balance. Furthermore, as shown in FIGS. 7(c) and 8(c), an extension gap G61 and a flexion gap G62 of the artificial knee joint 7 configured including the tibial insert 600 are defined. The gap between the extension gap G61 and the flexion gap G62 is defined as a gap balance.

Figure 9:
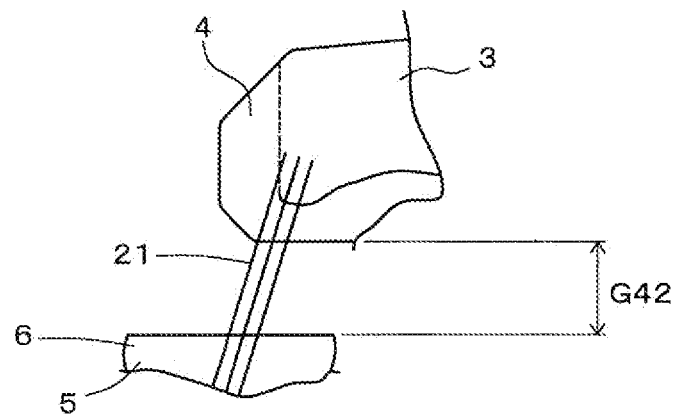
FIGS. 9(a), 9(b), and 9(c) are respectively views showing the states in which the artificial knee joint has been removed from FIGS. 8(a), 8(b), and 8(c).
Figure 9:
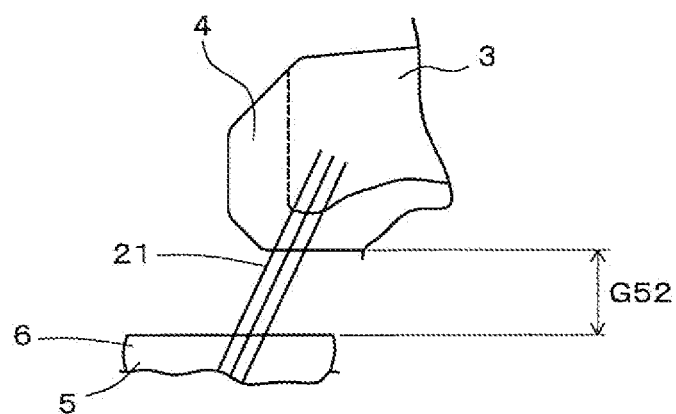
Figure 9:
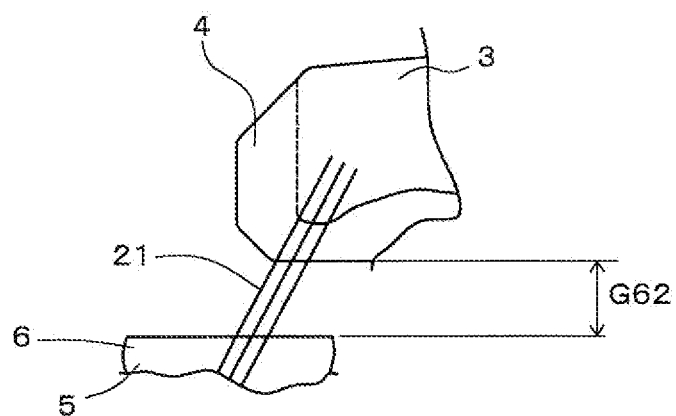

FIG. 9(a) is a view showing the state in which the artificial knee joint 7 has been removed from FIG. 8(a). Note that the antero-posterior position of the femur 3 in FIG. 9(a) is the position in which the post 402 and the cam portion 203 are in contact with each other in FIG. 8(a). Similarly, FIG. 9(b) is a view showing the state in which the artificial knee joint 7 has been removed from FIG. 8(b), and FIG. 9(c) is a view showing the state in which the artificial knee joint 7 has been removed from FIG. 8(c).

Referring to FIGS. 8(a), 8(b), and 8(c), the posts 402, 502, and 602 of the tibial inserts 400, 500, and 600 have different antero-posterior positions. As a result, the femur 3 when the femoral component 200 slides over the tibial insert 400 is positioned closer to the anterior side, by a distance α1, than the femur 3 when the femoral component 200 slides over the tibial insert 500. The femur 3 when the femoral component 200 slides over the tibial insert 500 is positioned closer to the anterior side, by a distance α2, than the femur 3 when the femoral component 200 slides over the tibial insert 600. Thus, if the posts 402, 502, and 602 have different antero-posterior positions, the relative position in the antero-posterior direction of two ends of a collateral ligament 21 can vary, and, thus, the tensile force of the collateral ligament 21 can be adjusted. As described above, FIGS. 9(a), 9(b), and 9(c) are respectively views showing the states in which the artificial knee joint 7 has been removed from FIGS. 8(a), 8(b), and 8(c), where the femur 3 has different antero-posterior positions with respect to the tibia 5, so that the collateral ligament 21 has different tensile forces. As a result, the force that moves the femur 3 and the tibia 5 closer to each other varies, and, thus, the flexion gap can be adjusted.

The gap balance in the artificial knee joint 7 is preferably close to a standard gap balance, which is a gap balance in a normal knee before the artificial knee joint 7 is installed, because the patient can feel a sense of naturalness. However, if the tibial insert 500 is uniformly applied to all patients, some patients will have a gap balance that is significantly different from the standard gap balance, and feel a sense of unnaturalness when flexing the knee.

The artificial knee joint implant 1 is provided with the plurality of tibial inserts 400, 500, and 600, and, thus, the gap balance can be adjusted. More specifically, as shown in FIGS. 7(a), 7(b), and 7(c), the extension gaps G41, G51, and G61 take the same value regardless of which tibial insert is selected to use from among the tibial insert 400, the tibial insert 500, and the tibial insert 600.

On the other hand, as described above with reference to FIGS. 8(a), 8(b), 8(c), 9(a), 9(b), and 9(c), when the femoral component 200 is in contact with the posts 402, 502, and 602 of the tibial inserts 400, 500, and 600, the flexion gaps G42, G52, and G62 take different values even at the same flexion angle.

As described above, the flexion gap varies between the cases using the tibial inserts 400, 500, and 600. Thus, the surgeon can select, during surgery, a tibial insert providing an optimum gap balance for the patient, from among the tibial inserts 400, 500, and 600.

Adjustment of the Collateral Ligament Position by Changing the Tibial Insert

As shown in FIGS. 7(a), 7(b), and 7(c), in the case of using the tibial inserts 400, 500, and 600, the distal portion 4 of the femur 3 has different positions in the antero-posterior direction with respect to the proximal portion 6 of the tibia 5 in an extension state. Specifically, the distal portion 4 in the case of using the tibial insert 400 is positioned closer to the anterior side, by a distance α3, than the distal portion 4 in the case of using the tibial insert 500. The distal portion 4 in the case of using the tibial insert 500 is positioned closer to the anterior side, by a distance α4, than the distal portion 4 in the case of using the tibial insert 600. Thus, the difference between the tibial inserts 400, 500, and 600 causes a variation in the relative position in the antero-posterior direction of the superior end and the inferior end of the collateral ligament 21 linking the femur 3 and the tibia 5. Accordingly, the surgeon can select the tibial insert 400, 500, or 600 such that the collateral ligament 21 is disposed at an optimum position for the patient. It should be noted that, typically, the position in the antero-posterior direction of the collateral ligament 21 can be made closer to the original position before the artificial knee joint 7 is installed, as the position of the post 402, 502, or 602 is closer to the anterior end of the corresponding plate 501. Accordingly, the patient can perform a more natural flexion movement.

As described above, an optimum tibial insert, with which the position in the antero-posterior direction of the collateral ligament 21 can be optimized, and, at the same time, the maximum flexion angle can be increased, is selected from among the tibial inserts 400, 500, and 600.

Adjustment of the Gap Balance by Changing the Femoral Component

Figure 10:
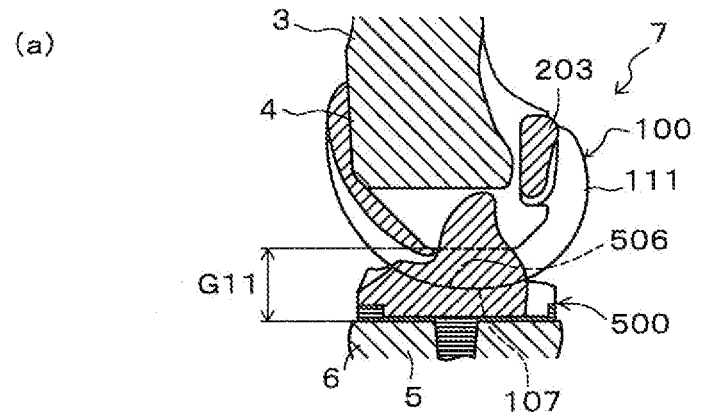
FIGS. 10(a), 10(b), and 10(c) are respectively cross-sectional views for illustrating a flexion movement of the artificial knee joint, showing the main portion viewed from a side, in a state where the flexion angle of the artificial knee joint is zero.
Figure 10:
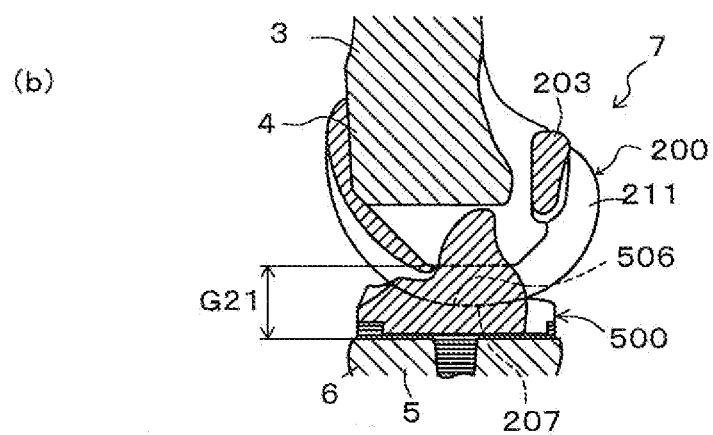
Figure 10:
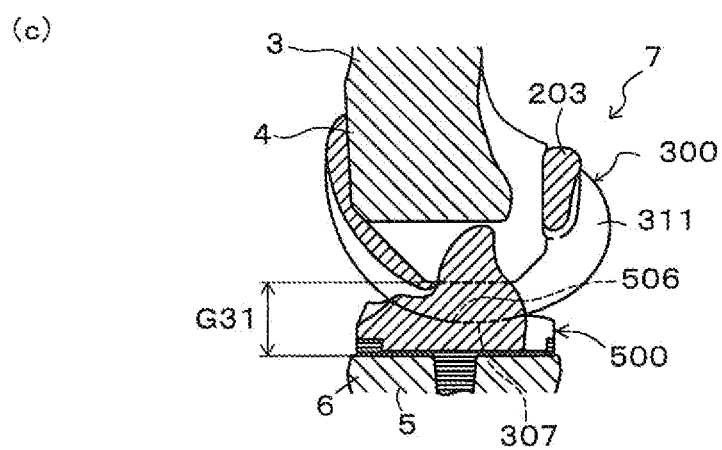

FIGS. 10(a), 10(b), and 10(c) are cross-sectional views for illustrating a flexion movement of the artificial knee joint 7, showing the main portion viewed from a side, in a state where the flexion angle of the artificial knee joint 7 is zero. FIGS. 10(a), 10(b), and 10(c) each show the case in which the artificial knee joint 7 includes a different femoral component. More specifically, FIG. 10(a) shows the case in which the artificial knee joint 7 includes the femoral component 100, FIG. 10(b) shows the case in which the artificial knee joint 7 includes the femoral component 200, and FIG. 10(c) shows the case in which the artificial knee joint 7 includes the femoral component 300.

Figure 11:
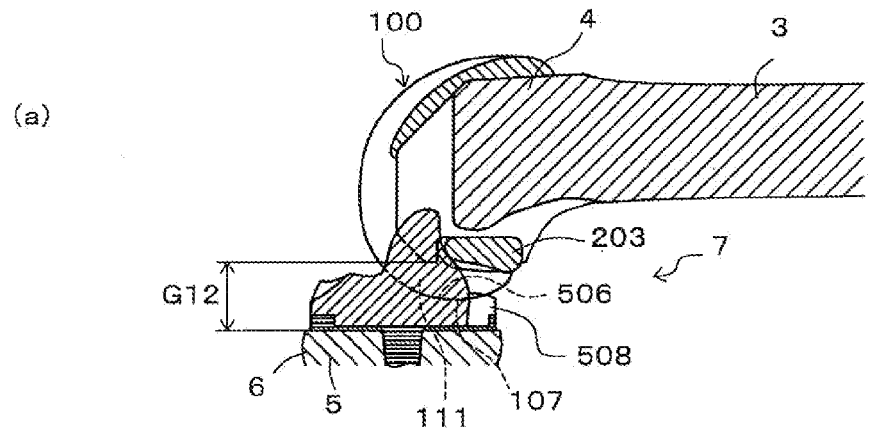
FIGS. 11(a), 11(b), and 11(c) are respectively cross-sectional views for illustrating a flexion movement of the artificial knee joint, showing the main portion viewed from a side, in a state where the flexion angle of the artificial knee joint is 90 degrees.
Figure 11:
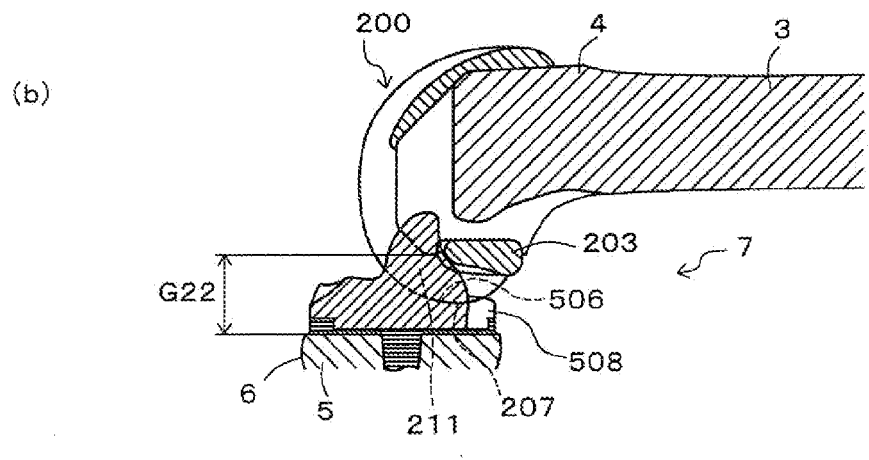
Figure 11:
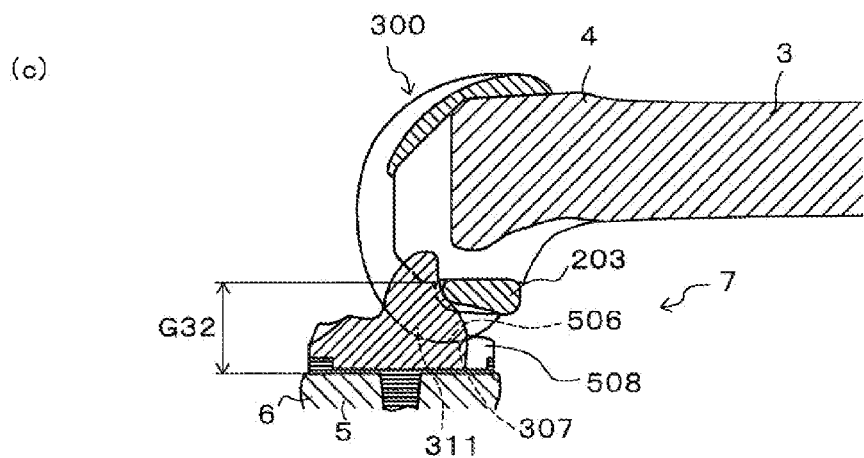

FIGS. 11(a), 11(b), and 11(c) are cross-sectional views for illustrating a flexion movement of the artificial knee joint 7, showing the main portion viewed from a side, in a state where the flexion angle of the artificial knee joint 7 is 90 degrees. FIGS. 11(a), 11(b), and 11(c) are views respectively corresponding to FIGS. 10(a), 10(b), and 10(c).

Figure 12:
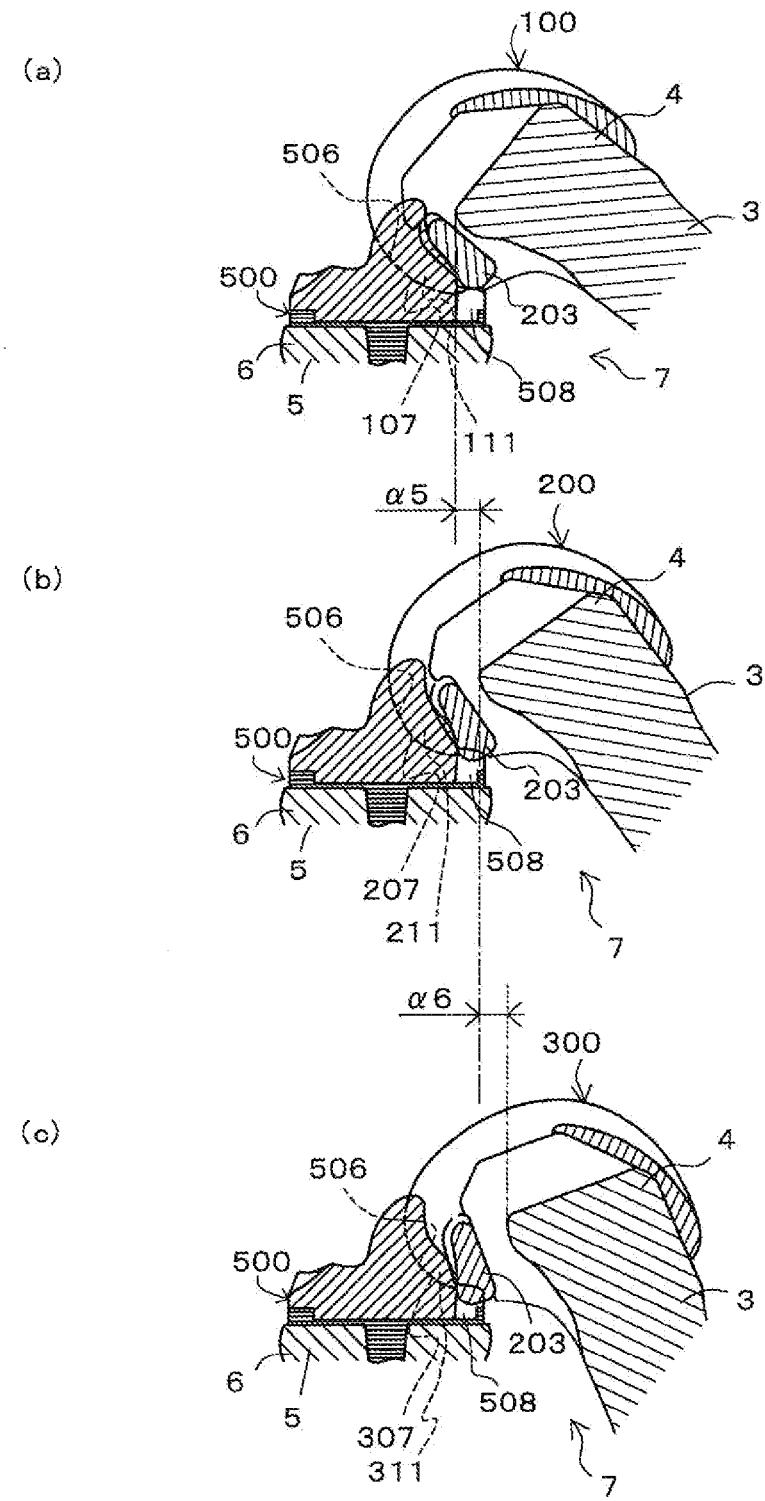
FIG. 12 shows cross-sectional views for illustrating a flexion movement of the artificial knee joint, showing the main portion viewed from a side, in a state where the flexion angle of the artificial knee joint is close to the maximum allowable flexion angle.

FIG. 12 shows cross-sectional views for illustrating a flexion movement of the artificial knee joint 7, showing the main portion viewed from a side, in a state where the flexion angle of the artificial knee joint 7 is close to the maximum allowable flexion angle. FIGS. 12(a), 12(b), and 12(c) are views respectively corresponding to FIGS. 10(a), 10(b), and 10(c). It should be noted that the same tibial insert 500 is used in FIG. 10 to FIG. 12.

The artificial knee joint implant 1 is provided with the plurality of femoral components 100, 200, and 300, and, thus, the gap balance can be adjusted. More specifically, as shown in FIGS. 10(a), 10(b), and 10(c), extension gaps G11, G21, and G31 take the same value regardless of which femoral component is selected to use from among the femoral component 100, the femoral component 200, and the femoral component 300.

On the other hand, as shown in FIGS. 11(a), 11(b), and 11(c), a flexion gap G12 in the case of using the femoral component 100, a flexion gap G22 in the case of using the femoral component 200, and a flexion gap G32 in the case of using the femoral component 300 take different values even at the same flexion angle. The reason for this is that when the cam portion 203 is in contact with the post 502, the posterior condyle 111 that is in contact with the tibial insert 500, the posterior condyle 211 that is in contact with the tibial insert 500, and the posterior condyle 311 that is in contact with the tibial insert 500 have different thicknesses.

As described above, the flexion gaps G12, G22, and G32 take different values even at the same flexion angle with respect to the tibial inserts 400, 500, and 600. Thus, the surgeon can select, during surgery, a femoral component providing an optimum gap balance for the patient, from among the femoral components 100, 200, and 300.

Adjustment of the Collateral Ligament Position by Changing the Femoral Component As shown in FIGS. 12(a), 12(b), and 12(c), when the artificial knee joint 7 is flexed at an allowable flexion angle, the position in the antero-posterior direction of the distal portion 4 of the femur 3 with respect to the proximal portion 6 of the tibia 5 varies between the femoral components 100, 200, and 300. Specifically, the position in the antero-posterior direction of the distal portion 4 of the femur 3 in the case of using the femoral component 100 is closer to the anterior side, by a distance α5, than the position in the antero-posterior direction of the distal portion 4 of the femur 3 in the case of using the femoral component 200. The position in the antero-posterior direction of the distal portion 4 of the femur 3 in the case of using the femoral component 200 is closer to the anterior side, by a distance α6, than the position in the antero-posterior direction of the distal portion 4 of the femur 3 in the case of using the femoral component 300. Thus, the position in the antero-posterior direction of the collateral ligament 21 (see FIG. 7) linking the femur 3 and the tibia 5 varies between the femoral components 100, 200, and 300. Accordingly, the surgeon can select the femoral components 100, 200, or 300 such that the collateral ligament 21 is disposed at an optimum position for the patient when the artificial knee joint 7 is flexed at the allowable flexion angle.

As described above, an optimum femoral component, with which the position in the antero-posterior direction of the collateral ligament 21 can be optimized, and, at the same time, the allowable flexion angle can be increased, is selected from among the femoral components 100, 200, and 300.

Accordingly, the surgeon selects an optimum femoral component for the patient from among the femoral components 100, 200, and 300, and selects an optimum tibial insert for the patient from among the tibial inserts 400, 500, and 600 (see FIG. 7).

As described above, according to the artificial knee joint implant 1, the tibial inserts 400, 500, and 600 are respectively provided with the posts 402, 502, and 602 having different antero-posterior positions with respect to the tibial joint face 506. Accordingly, an optimum tibial insert can be selected from among the plurality of tibial inserts 400, 500, and 600 and attached to the tibia 5 such that the antero-posterior position of the post is optimum for the patient. Accordingly, the antero-posterior position of the post can be optimized for the patient. If the antero-posterior position of the post is adjusted, the tensile force of the collateral ligament 21 of the patient can be adjusted. As a result, a more proper gap balance can be achieved between an extension gap, which is a gap between the distal portion 4 of the femur 3 and the proximal portion 6 of the tibia 5 when the patient's knee is straightened, and a flexion gap, which is a gap between the distal portion 4 of the femur 3 and the proximal portion 6 of the tibia 5 when the patient's knee is flexed. Accordingly, a stable deep flexion movement can be realized. Moreover, the post can be disposed as close to the posterior side as possible, while satisfying the condition that the collateral ligament 21 is disposed closer to the anterior side so that the patient can naturally flex the knee. Accordingly, when the cam portion 203 of one of the femoral components 100, 200, and 300 and one of the posts 402, 502, and 602 slide over each other, the flexion angle until the one of the femoral components 100, 200, and 300, or the femur 3 impinges on the one of the tibial inserts 400, 500, and 600 can be increased. As a result, the deep flexion performance can be improved so that the femur 3 can be flexed at a larger flexion angle with respect to the tibia 5.

Moreover, contrary to the method (i) described above, it is not necessary to perform the operation that peels away (releases) as appropriate, from the femur and the tibia, soft tissue around the artificial knee joint, such as the collateral ligament of the patient, in order to adjust the gap balance. Thus, it is not necessary to perform the release operation which the surgeon has to be careful so as not to damage blood vessels and nerves around the soft tissue. Accordingly, the burden on the surgeon and the patient, resulting from the operation that installs the artificial knee joint implant 1, can be reduced.

Furthermore, contrary to the method (ii) described above, it is not necessary to change the installation position of the femoral components 100, 200, and 300 on the femur 3 in each case in order to adjust the gap balance. Thus, the degree of freedom in selecting the position where to form the bone resection surface 10 on the femur 3 can be increased, and, thus, it is not necessary to form a bone resection surface having a shape that requires the femur 3 to be notched. Accordingly, no stress resulting from the notch is concentrated on the femur 3, and a decrease in the strength of the femur 3 can be suppressed, and, thus, the burden on the patient can be reduced. Moreover, it is not necessary to change the position of the femoral components 100, 200, and 300 in order to adjust the gap balance. Thus, one of the femoral components 100, 200, and 300 can be disposed at a proper position with respect to the patella. As a result, a good sliding state can be achieved between one of the femoral components 100, 200, and 300 and the patella, and the patellar tracking disorder can be suppressed. Accordingly, the patient can naturally flex the knee.

Furthermore, contrary to the method (iii) described above, it is not necessary to change the whole size of the femoral component in order to adjust the gap balance. Thus, it is not necessary to increase or reduce the size of the femoral components 100, 200, and 300 in order to adjust the gap balance. Accordingly, the bone resection amount of the femur 3 does not have to be increased, and extra bone resection operation does not have to be performed, and, thus, the burden on the surgeon and the patient can be reduced. Moreover, the problem that a pressure is applied by a large femoral component to soft tissue of the patient can be suppressed, and, thus, the burden on the patient can be reduced.

Furthermore, contrary to the method (iv) described above, it is not necessary to change the thickness of the tibial inserts 400, 500, and 600 in order to adjust the gap balance. Thus, the height position of a joint line, which is a portion where one of the tibial inserts 400, 500, and 600 and one of the femoral components 100, 200, and 300 are in contact with each other, is not affected by the gap balance adjustment. As a result, the relative height position between one of the femoral components 100, 200, and 300 and the patella can be made constant regardless of whether or not the gap balance is adjusted. That is to say, how one of the femoral components 100, 200, and 300 and the patella relatively slide over each other can be made constant regardless of whether or not the gap balance is adjusted. As a result, the above-described patellar tracking disorder and the like can be suppressed.

Furthermore, according to the method (v) described above, a femoral component with a posterior condyle having a different thickness is selected in order to adjust the gap. According to this method, the balance of the relative positions between the collateral ligament and the femoral component cannot be adjusted. On the other hand, according to the artificial knee joint implant 1, the relative positions between the collateral ligament 21 and the femoral component 100, 200, or 300 can be adjusted through adjustment applying one of the antero-posterior positions of the posts 402, 502, and 602 of the tibial inserts 400, 500, and 600. As a result, the femur 3 can be flexed with respect to the tibia 5 at a position close to the original position in the living body, and, thus, the patient's knee can be flexed at a natural posture.

Accordingly, with application of the artificial knee joint implant 1, the gap balance can be adjusted in order to realize a stable deep flexion movement, the burden on the surgeon and the patient can be reduced, and the patient can perform a natural flexion movement.

Furthermore, according to the artificial knee joint implant 1, the femoral components 100, 200, and 300 are respectively provided with the fixing faces 205 having the same shape and the posterior condyles 111, 211, and 311 having different thicknesses.

Accordingly, an optimum femoral component can be selected from among the plurality of femoral components 100, 200, and 300 such that a proper gap balance can be achieved between the femur 3 and the tibia 5, and, at the same time, the collateral ligament 21 can be disposed so as to realize natural flexion of the knee. For example, if the patient has a small flexion gap, the gap balance can be adjusted by using one of the femoral components 100 and 200 with the posterior condyles having smaller thicknesses. Furthermore, if the patient has a large flexion gap, the gap balance can be adjusted by using one of the femoral components 200 and 300 with the posterior condyles having larger thicknesses. Furthermore, in order to arrange the position of the collateral ligament 21 closer to the anterior side when the knee is flexed, a femoral component with a posterior condyle having a smaller thickness is preferably selected to use from among the femoral components 100, 200, and 300. Moreover, the range in which the gap balance can be adjusted can be increased, and the gap balance can be finely controlled, by combining the femoral component with one of the tibial inserts 400, 500, and 600 with the posts 402, 502, and 602 having different antero-posterior positions. Moreover, the arrangement of the collateral ligament 21 can be more easily adjusted, and a better state can be provided for the user, by combining the femoral components 100, 200, and 300 with the posterior condyles 111, 211, and 311 having different thicknesses and the tibial inserts 400, 500, and 600 with the posts 402, 502, and 602 having different antero-posterior positions. Accordingly, a femoral component (one of the femoral components 100, 200, and 300) with a posterior condyle having an optimum thickness can be used such that a proper gap balance can be achieved, and, at the same time, the arrangement of the collateral ligament 21 can be optimized.

Furthermore, according to the artificial knee joint implant 1, the femoral joint faces 107, 207, and 307 on the posterior condyles 111, 211, and 311 respectively in the plurality of femoral components 100, 200, and 300 have different radii of curvature. In this manner, with a simple configuration providing different radii of curvature, the posterior condyles 111, 211, and 311 of the femoral components 100, 200, and 300 can have different thicknesses.

Furthermore, the posts 402, 502, and 602 of the plurality of tibial inserts 400, 500, and 600 have the same shape. Thus, during surgery for installing the artificial knee joint 7, the movement of the femur 3 with respect to the tibia 5 when changing the type of tibial insert from among the tibial inserts 400, 500, and 600 can be easily predicted. Thus, the surgeon can easily select an optimum tibial insert for the patient from among the tibial inserts 400, 500, and 600. As a result, the duration of surgery can be shortened, and, thus, the burden on the surgeon and the patient can be further reduced.

Furthermore, according to the artificial knee joint implant 1, the tibial tray 2 is configured as a member independent of the tibial inserts 400, 500, and 600. Accordingly, the tibial tray 2 can be used to fix one of the tibial inserts 400, 500, and 600 to the proximal portion 6 of the tibia 5. Furthermore, a stable deep flexion movement between the femur 3 and the tibia 5 is realized by providing the tibial inserts 400, 500, and 600 with the posts 402, 502, and 602 having different antero-posterior positions. Accordingly, it is not necessary to change the shape of the tibial tray 2 in order to realize a stable deep flexion movement. Thus, it is not necessary to change the shape of the bone resection surface 10 of the tibia 5 to which the tibial tray 2 is to be fixed, in order to realize a stable deep flexion movement. Accordingly, the burden on the surgeon and the patient can be reduced.

In the description above, an embodiment of the present invention was described, but the present invention is not limited thereto, and various modifications may be made within the scope recited in the claims. For example, the following modifications are possible.

Figure 13:
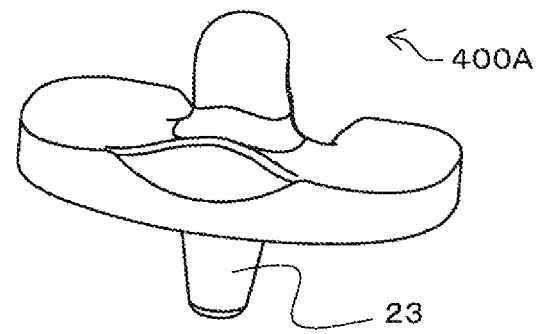
FIGS. 13(a) and 13(b) are perspective views respectively showing modified examples of the tibial component and the tibial tray.
Figure 13:
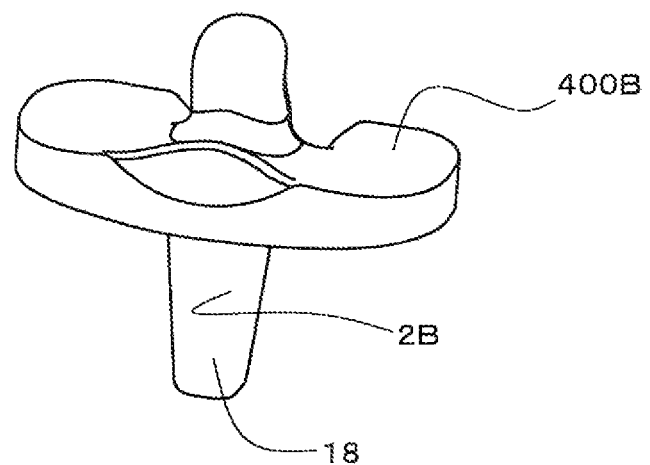

(1) Although the foregoing embodiment was described using an example in which the superior face of the tibial tray and the inferior face of the tibial component are flat, there is no limitation to this. For example, as shown in FIG. 13(*a*), a recess portion 16 oriented to the inferior side may be formed in a tibial tray 2A, and a projection portion 23 formed on the inferior face of a tibial insert 400A may be inserted into the recess portion 16. The same can be applied to the tibial inserts 500 and 600.

(2) Although the foregoing embodiment was described using an example in which the tibial tray and the tibial component are configured as members independent of each other, there is no limitation to this. For example, as shown in FIG. 13(*b*), a tibial insert 400B and a tibial tray 2B having a projection portion 18 oriented to the inferior side may be configured as one piece made of a single material. The same can be applied to the tibial insert 500 and the tibial tray 2, and the same can be applied to the tibial insert 600 and the tibial tray 2.

(3) Furthermore, a so-called "mobile" tibial component may be used as the tibial component of the present invention.

(4) Although the foregoing embodiment was described using an example in which the number of tibial components is three, there is no limitation to this. For example, the number of tibial components included in the artificial knee joint implant may be any number that is two or more.

(5) Although the foregoing embodiment was described using an example in which the number of femoral components is three, there is no limitation to this. For example, the number of femoral components included in the artificial knee joint implant may be any number that is one or more. If the number of femoral components included in the artificial knee joint implant is two or more, a better femoral component can selected.

(6) Although the foregoing embodiment was described using an example in which the femoral joint face of the posterior condyle and the femoral joint face of the superior condyle have, on the whole, a plurality of radii of curvature, there is no limitation to this. For example, the femoral joint face of the posterior condyle and the femoral joint face of the superior condyle may have, on the whole, a single radius of curvature.

(7) Although the foregoing embodiment was described using an example in which the posts of the tibial inserts have the same shape, there is no limitation to this. For example, the posts of the tibial inserts may have different shapes.

EXAMPLE

An artificial knee joint implant similar to that shown in FIG. 1 was prepared for Example. Furthermore, an artificial knee joint implant having one tibial insert and one femoral component was prepared for Comparative Example. The configuration obtained by selecting a tibial insert and a femoral component that were optimum for the patient from among those in Example, and the configuration of Comparative Example were each attached to the tibia and the femur of the patient, and examined by performing computer simulation on the movement of the patient's knee.

Figure 14:
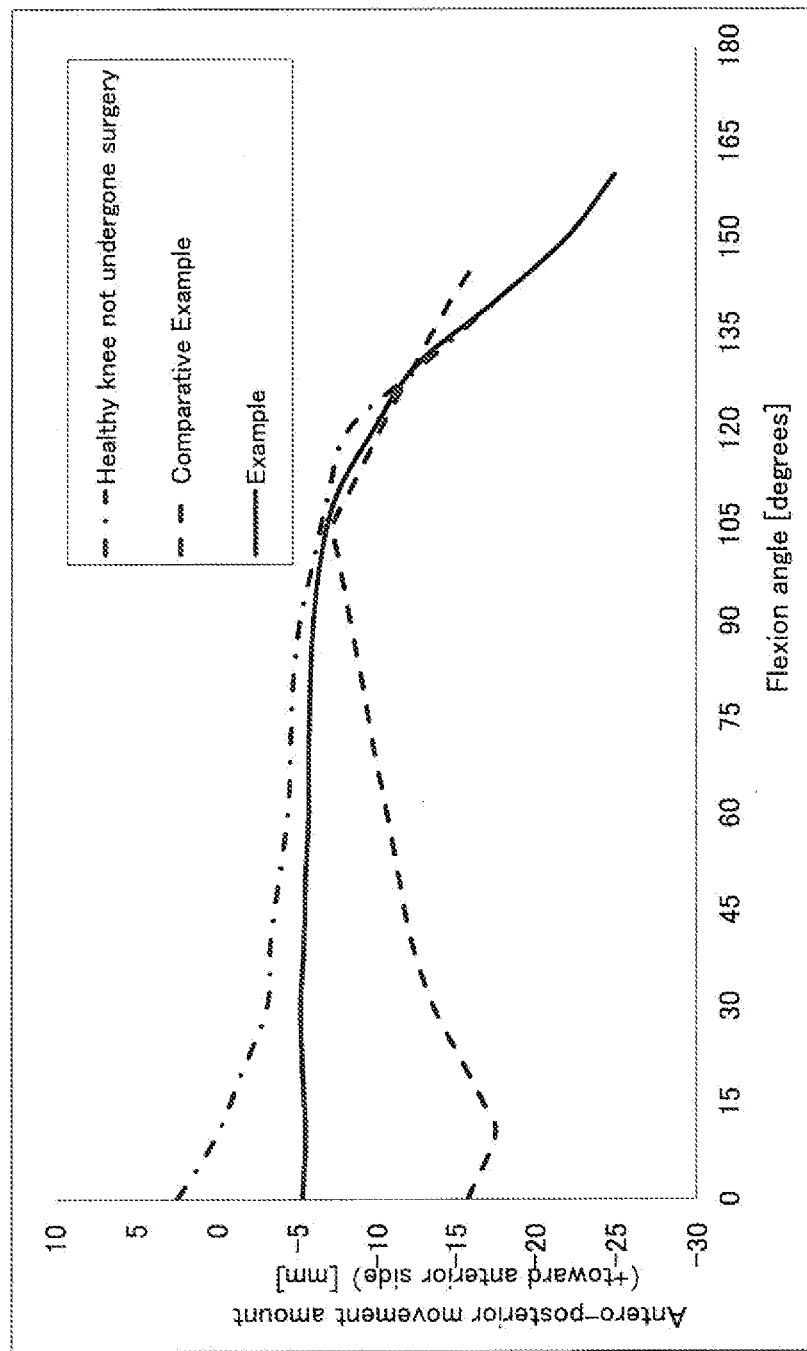
FIG. 14 is a graph showing the experimental results of Example and Comparative Example.

FIG. 14 shows the results. FIG. 14 shows the relationship between the flexion angle of the artificial knee joint and the antero-posterior position of the distal portion of the femur with respect to the central axis of the tibia. In the graph in FIG. 14, the solid line indicates the result of Example, the broken line indicates the result of Comparative Example, and the dashed dotted line indicates the movement of the normal knee of the patient without attachment of an artificial knee joint.

That is to say, a movement closer to that indicated by the dashed dotted line is a more natural movement. As is clear from FIG. 14, Comparative Example resulted in a movement completely different from the movement of the normal knee of the patient at a small flexion angle. On the other hand, Example clearly achieved a movement extremely close to the movement of the normal knee of the patient at any flexion angle. As described above, it was proven that Example is preferable for achieving a movement of the knee without a sense of unnaturalness for the patient.

INDUSTRIAL APPLICABILITY

The present invention is widely applicable as an artificial knee joint implant for use in surgery for removing an anterior cruciate ligament and a posterior cruciate ligament of a patient, and replacing the knee joint of the patient by an artificial knee joint.

LIST OF REFERENCE NUMERALS

1 Artificial knee joint implant
2 Tibial tray
3 Femur
4 Distal portion
5 Tibia
6 Proximal portion
7 Artificial knee joint
10 Bone resection surface
18 Tibial component
100, 200, 300 Femoral component
111, 211, 311 Posterior condyle
112, 212, 312 Superior condyle
203 Cam portion
205 Fixing face
107, 207, 307 Femoral joint face
400, 500, 600 Tibial insert
402, 502, 602 Post
506 Tibial joint face

The invention claimed is:

1. An artificial knee joint implant for use in surgery for removing an anterior cruciate ligament and a posterior cruciate ligament of a patient, and replacing a knee joint of the patient by an artificial knee joint, comprising:
   a femoral component that is to be attached to a distal portion of a femur of the patient; and
   a tibial insert that is to be attached to a proximal portion of a tibia of the patient;
   wherein the femoral component includes:
      a fixing face that is to be fixed to a bone resection surface formed on the distal portion;
      two femoral joint faces that are curved toward the outer side of the femoral component;
      a cam portion that is disposed between posterior portions of the two femoral joint faces;
      posterior condyles that are arranged posterior to the fixing face, and form part of the two femoral joint faces; and
      superior condyles that are arranged superior to the posterior condyles, and form part of the two femoral joint faces;
   the tibial insert includes:
      two tibial joint faces that can slide over the two femoral joint faces; and
      a post that projects from between the two tibial joint faces to a space between the two femoral joint faces, and can be brought into contact with the cam portion;
   a plurality of tibial inserts respectively provided with posts having different antero-posterior positions with respect to the tibial joint faces are provided as the tibial insert, and one of the plurality of tibial inserts is to be permanently attached to the proximal portion of the tibia of the patient; and
   a plurality of femoral components respectively provided with fixing faces having the same shape and posterior condyles having different thicknesses are provided as the femoral component, and one of the plurality of femoral components is to be permanently attached to the distal portion of the femur of the patient.

2. The artificial knee joint implant according to claim 1, wherein the femoral joint faces on the posterior condyles respectively in the plurality of femoral components have different radii of curvature.

3. The artificial knee joint implant according to claim 1, further comprising:
   a tibial tray that is to be fixed to the proximal portion of the tibia, supports the tibial insert, and constitutes a tibial component in cooperation with the tibial insert;
   wherein the tibial tray is formed in one piece with the tibial insert, or is formed as a member independent of the tibial insert and is fixed to the tibial insert.

4. An artificial knee joint implant for use in surgery for removing an anterior cruciate ligament and a posterior cruciate ligament of a patient, and replacing a knee joint of the patient by an artificial knee joint, comprising:
   a femoral component that is to be attached to a distal portion of a femur of the patient; and
   a tibial insert that is to be attached to a proximal portion of a tibia of the patient;
   wherein the femoral component includes:
      a fixing face that is to be fixed to a bone resection surface formed on the distal portion;
      two femoral joint faces that are curved toward the outer side of the femoral component;
      a cam portion that is disposed between posterior portions of the two femoral joint faces;
      posterior condyles that are arranged posterior to the fixing face, and form part of the two femoral joint faces; and
      superior condyles that are arranged superior to the posterior condyles, and form part of the two femoral joint faces;
   the tibial insert includes:
      two tibial joint faces that can slide over the two femoral joint faces; and
      a post that projects from between the two tibial joint faces to a space between the two femoral joint faces, and can be brought into contact with the cam portion;
   a plurality of tibial inserts respectively provided with posts having different antero-posterior positions with respect to the tibial joint faces are provided as the tibial insert, and one of the plurality of tibial inserts is to be permanently attached to the proximal portion of the tibia of the patient; and
   the posts of the plurality of tibial inserts have the same front shape or rear shape.

5. The artificial knee joint implant according to claim 4, further comprising:
   a tibial tray that is to be fixed to the proximal portion of the tibia, supports the tibial insert, and constitutes a tibial component in cooperation with the tibial insert;
   wherein the tibial tray is formed in one piece with the tibial insert, or is formed as a member independent of the tibial insert and is fixed to the tibial insert.

* * * * *